US009188590B2

(12) United States Patent  
Lacombe et al.

(10) Patent No.: US 9,188,590 B2  
(45) Date of Patent: Nov. 17, 2015

(54) LABELED TRANSITION METAL COMPLEXES

(75) Inventors: Marie Lacombe, Charenton-le-Pont (FR); Franciscus Johannes Opdam, Alkmaar (NL); Eduard Gerhard Talman, Diemen (NL); Jacky Theo Maria Veuskens, Hasselt (BE)

(73) Assignee: LEICA BIOSYSTEMS NEWCASTLE LTD., Newcastle Upon Tyne (GB)

( * ) Notice: Subject to any disclaimer, the term of this patent is extended or adjusted under 35 U.S.C. 154(b) by 1759 days.

(21) Appl. No.: 11/721,189

(22) PCT Filed: Dec. 1, 2005

(86) PCT No.: PCT/NL2005/000824  
§ 371 (c)(1),  
(2), (4) Date: Feb. 26, 2010

(87) PCT Pub. No.: WO2006/062391  
PCT Pub. Date: Jun. 15, 2006

(65) Prior Publication Data  
US 2010/0155590 A1 Jun. 24, 2010

(30) Foreign Application Priority Data  
Dec. 8, 2004 (EP) .................................. 04078328

(51) Int. Cl.  
C07F 15/00 (2006.01)  
C07F 5/00 (2006.01)  
G01N 33/58 (2006.01)

(52) U.S. Cl.  
CPC ............ *G01N 33/58* (2013.01); *C07F 15/0093* (2013.01)

(58) Field of Classification Search  
CPC .............. C07F 15/00; C07F 5/00; C07F 9/02; C07K 2/00  
USPC ........ 514/188, 212.01; 530/300, 395; 436/84, 436/546; 536/23.1, 24.3, 26.6  
See application file for complete search history.

(56) References Cited

U.S. PATENT DOCUMENTS

| | | | | |
|---|---|---|---|---|
| 6,133,038 | A * | 10/2000 | Houthoff et al. | 436/84 |
| 6,825,330 | B2 * | 11/2004 | Braman et al. | 536/23.1 |
| 2002/0013306 | A1 * | 1/2002 | Lowe | 514/188 |

FOREIGN PATENT DOCUMENTS

| | | |
|---|---|---|
| EP | 0870770 | 10/1998 |
| EP | 1262778 | 4/2002 |
| EP | 1505394 | 2/2005 |
| WO | 9532428 | 11/1995 |

OTHER PUBLICATIONS

Joseph F. Michalec et al. Long-Lived Emissions from 4'-substituted Pt(trpy)Cl+ Complexes bearing Aryl Groups. Influence of Orbital Parentage, Inorg. Chem. 2001, 40, 2193-2200.*  
Daniel W. Pack et al. Ligand-induced reorganization and assembly in synthetic lipid membranes, Supramolecular Science, 4, 3-10, 1997.*  
Hui Chao et. al., DNA binding studies of ruthenium(II) complexes containing asymmetric tridentate ligands, Journal of Inorganic Biochemistry, 92, 165-170, 2992.*  
Andrew C. Benniston et al. The photophysical porperties of a pyrene-thiophene-terpyridine conjugate and of its zinc(II) and ruthem=nium(II) complexes, Phys. Chem.Chem.Phys. 6, 51-57, 2004.*  
S. Murali et al. New mixed ligand complexes of ruthenium(II) that incorporate a modified phenanthroline ligand: Synthesis, spectral characteriazation and DNA binding, Proc. Indian Acamd. Sci. (Chem. Sci) vol. 114 (4) 403-415, 2002.*  
Eva Marie A. Ratilla et al. A Transition-Metal Chromophore as a New, Sensitive Spectroscopic Tag for Proteins. Selective Covalent Labeling of Histidine Residues in Cytochromes c with Chloro(2,2':6',2"-terpyridine) Platinum(II) Chloride, J. Am. Chem. Soc. vol. 109(15), 4592-4599, 1987.*  
Karin A. Stephenson et al. A New Strategy for the Preparation of Peptide-Targeted Radiopharmaceuticals Based on an Fmoc-Lysine-Derived Single Amino Acid Chelate (SAAC). Automated Solid-Phase Synthesis, NMR Characterization, and in Vitro Screening of fMLF(SAAC) and fMLF[(SAAC-Re(CO)3)+]G, Bioconjugate Chem. 2004, 15, 128-136.*  
McDonnell, James, "Surface Plasmon Resonance: Towards an Understanding of the Mechanisms of Biological Molecular Recognition", Current Opinion in Chemcial Biology, vol. 5, pp. 572-577; 2001.  
Rich, et al., "Advances in Surface Plasmon Resonance Biosensor Analysis", Current Opinion in Biotechnology, vol. 11, pp. 54-61; 2000.  
Mann, et al., "Analysis of Proteins and Proteomes by Mass Spectrometry", Annu. Rev. Biochem, vol. 70, pp. 437-473; 2001.  
Chakraborty, et al., "Global Internal Standard Technology for Comparative Proteomies", Journal of Chromatography A., vol. 949, pp. 173-184; 2002.

(Continued)

*Primary Examiner* — Michael G Hartley  
*Assistant Examiner* — Jagadishwar Samala  
(74) *Attorney, Agent, or Firm* — Hoffmann & Baron, LLP

(57) ABSTRACT

The invention relates to a labeled transition metal complex comprising a transition metal atom, a reactive moiety for allowing a chemical or biological entity to become attached to the transition metal atom, an inert tridentate moiety as a stabilizing bridge, and a marker. The invention also relates to a labeled chemical or biological entity comprising a chemical or biological entity which is attached to said labeled transition metal complex, to the use of said complex for creating a defined shift in the molecular mass of said entity in order to facilitate mass spectrometric analysis of said entity, to methods for rendering chemical or biological entities distinguishable by mass spectrometry as well as to methods for mass spectrometric analysis of the chemical or biological entities. In addition, the present invention also relates to a set of at least two of said transition metal complexes of different molecular mass, to transition metal complexes comprising different stable isotopes, to chemical or biological entities obtained by a method of the invention and to a kit of parts supporting the use and/or methods of the invention.

11 Claims, 17 Drawing Sheets

(56) References Cited

OTHER PUBLICATIONS

Chen, et al., "Interconversion Between S-and N-Bound L-Methionine Adducts of Pt(dien)2+ (dien=diethylenetriamine) via dien ring-opened intermediates", J. Chem. Soc., Dalton Trans., pp. 1503-1508; 1998.

Green, et al., "Surface Plasmon Resonance Analysis of Dynamic Biological Interactions with Biomaterials", Biomaterials, vol. 21, pp. 1823-1835; 2000.

Gygi, et al., "Mass Spectrometry and Proteomics", Current Opinion in Chemical Biology, vol. 4, pp. 89-494; 2000.

Michalec, et al., "Multiple Ligand-Based Emissions From A Platinum II Terpyridine Complex Attached to Pyrene", Chem., vol. 39, pp. 2708-2709; 2000.

Michalec, et al., "Long-Lived Emissions From 4'-Substituted Pt(trpy)Cl+Complexes Bearing Aryl Groups Influence of Ortbital Parentage", Inorg. Chem., vol. 40, pp. 2193-2200;2001.

Patton, Wayne F., "Detection Technologies in Proteome Analysis", Journal of Chromatography B., vol. 771, pp. 3-31, 2002.

Socorro, et al., "Kinetics of Formation and Stability of [Pt(dien)]2+ Complexes With Octamer and 14-mer DNA Oligonucleotides Containing a GG Sequence", JBIC, vol. 4, pp. 32-38; 1999.

Ruddock, et al., "Chloro(2,2':6',2''-terpyridine) Platinum Inhibition of the Renal Na+,K+-ATPase", AJP-Cell Physiol, vol. 284, pp. 1584-1592; 2003.

Shen, et al., "Isolation and Isotope Labeling of Cysteine—And Methionine—Containing Tryptic Peptides", The American Society for Biochemistry and Molecular Biology, Inc., pp. 315-324; 2003.

Van Der Schilden, et al., "A Highly Flexible Dinuclear Ruthenium(II)-Platinum(II) Complex: Crystal Structure and Binding to 9-Ethylguanine", Angew. Chem. Int. Ed., vol. 43, pp. 5668-5670; 2004.

Wee, et al., "Gas-Phase Studies on the Reactivity of the Azido(diethylenetriamine)Platinum(II)Cation and Derived Species", Aust. J. Chem., vol. 56, pp. 1201-1207; 2003.

Wee, et al., "Gas-phase Ligand Loss and Ligand Substition Reactions of Platinum II Complexes of Tridentate Nitrogen Donor Ligands", Rapid Commun. Mass Spectrum, vol. 18, pp. 1221-1226; 2004.

Zang, et al., "A Convenient Synthesis of 15 N-Labeled Diethylenetriamine [(15N)Dien] and Ethylenediamine [(15N) En]", Synthesis, pp. 410-412; 1997.

Regnier, et al., "Comparative Proteomics Based on Stable Isotope Labeling and Affinity Selection", J. Mass Spectrom, vol. 37, pp. 133-145; 2002.

Rabilloud, Thierry, "Detecting Proteins Separated by 2-D Gel Electrophoresis", Analytical Chemistry, pp. 48-55; 2000.

Patterson, et al., "Proteomics: The First Decade and Beyond", Nature Genetics Supplement, vol. 33, pp. 311-323; 2003.

Pennington, et al., "Proteome Analysis: From Protein Characterization to Biological Function", Cell Biology, vol. 7, pp. 168-173; 1997.

Goshe, et al., "Stable Isotope-Coded Proteomic Mass Spectrometry", Current Opinion in Biotechnology, vol. 14, pp. 101-109; 2003.

Peters, et al., "A Novel Multifunctional Labeling Reagent for Enhanced Protein Characterization With Mass Spectrometry", Rapid Commun. Mass Spectrum, vol. 15, pp. 2387-2392; 2001.

Dale, et al., "Direct Covalent Mercuration of Nucleotides and Polynucleotides", Biochemistry, vol. 14, pp. 2447-2457;1975.

Cagney, et al., "De Novo Peptide Sequencing and Quantitative Profiling of Complex Protein Mixtures Using Mass-Coded Abundance Tagging", Nature Biotechnology, vol. 20, pp. 163-170; 2002.

Gygi, et al., "Quantitative Analysis of Complex Protein Mixtures Using Isotope-Coded Affinity Tags", Nature America Inc., vol. 17, pp. 994-998; 1999.

Bauer, et al., "Affinity Purification-Mass Spectrometry", Eur. J. Biochem, vol. 270, pp. 570-578; 2003.

* cited by examiner

Figure 1: Labelling of total human DNA (500 – 1500 bp) with Bio-BOC-Pt or Bio-APET-Ru. Incubation time and temperatures as DNA labelling parameters. Direct spotting of labelled DNA and detection with anti-Biotin-AP (NBT/BCIP).

Figure 2: Labelling of total human DNA (500 – 1500 bp) with DNP-BOC-Pt or DNP-APET-ULS. Temperatures as DNA labelling parameter. Direct spotting of labelled DNA and detection with anti-Biotin-AP (NBT/BCIP). Detection limit of standard DNP-ULS (3 pg) was set to 100% (relative reactivity).

Figure 3: Result of IgA capture ELISA of whole serum labelled with Cy5- labelling reagents.

Figure 4: ESI-MS spectrum of Pt[dien Cl⁻]Cl⁻.
The most abundant molecular ion obtained for the Pt[dien Cl⁻]Cl⁻ compound has a molecular ion [M1+] at m/z = 334.

SCHEME 1: route to 3

Figure 6  SCHEME 2: route to labeled Pt(II) complexes from 3

SCHEME 3: route to 8

SCHEME 4: route to labeled Pt(II) complexes from 8

Scheme 5: Synthesis of N₃ trans-C3 tridentate

Western Blot of HELA lysate labeled with N3 trans-Bio ULS

0.5, 1, 2, 4 or 16 µg labeling compound per 50 µg protein, respectively.

Western Blot of a mixture of six proteins labeled with N3 trans-Flu ULS (4b)

Human metaphase hybridized with a 1.q12 DNA probe labeled with $N_3$ trans-Flu ULS (4b); DNA is counterstained with DAPI

Scheme 6: Synthesis of the N₃ cis-C2 tridentate

Western Blot of 6-protein mixture labeled with N3-cis Bio-ULS (5)

Synthesis of 7-complexation with potassium tetrachloroplatinate

Scheme 7: Synthesis of the N₃ trans-C2 tridentate

Scheme 8: Synthesis of the NS₂ trans-C2 tridentate

LABELED TRANSITION METAL COMPLEXES

This application is the U.S. National Phase of, and Applicants claim priority from, International Application Number PCT/NL2005/000824 filed 1 Dec. 2005 and European Patent Application bearing Serial No. EP 04078328.4 filed 8 Dec. 2004, which are incorporated herein by reference.

BACKGROUND OF THE INVENTION

The invention relates to labeled transition metal complexes, labeled chemical or biological entities comprising such complexes, methods for preparing said labeled chemical or biological entities, as well as to specific uses of such transition metal complexes.

The labeling of bio-organic molecules, such as DNA molecules, is desirable for applications in fields such as recombinant DNA technology. In many cases, however, one wishes not to label the nucleic acid macromolecule, but to label a certain nucleotide. The main purpose for labeling nucleotides is that these labeled nucleotides can be incorporated in nucleic acid molecules. This way, the location of the label on the resulting polynucleic acid can be influenced, which is not possible when a label is attached to the macromolecule.

It is known that nucleotides can be linked in a sufficient way to a label by means of a cis-platinum complex. However, such labeled nucleotides are not satisfactorily built in into DNA molecules by DNA polymerase, if at all.

The available alternative methods for labeling a nucleotide, which can be incorporated into a polynucleic acid are the more conventional methods for labeling. However, these methods also have a major disadvantage as they are not suitable for labeling any nucleotide. In some cases, for instance, when only a few residues of a certain nucleotide are present in a certain polynucleic acid, or when the terminating nucleotide residue of a polynucleic acid is to be labeled, it is desired to be able to label any nucleotide. An example of such a conventional method has been described by Dale et al., Biochemistry, 14, (1975), 2447-2457, which method involves direct covalent mercuration as a labeling technique. Dale et el. report that cytosine and uracil may be mercurated at their C5-position under mild conditions. However, they also report that for adenine, thymine and guanine bases negative results were obtained.

Thus, there is a need for a universal labeling system, which is excellent for linking labels and bio-organic molecules, including all different nucleotides, and which also makes it possible to enzymatically build in any nucleotide labeled through said labeling system in a polynucleic acid in an efficient manner.

BRIEF SUMMARY OF THE INVENTION

The invention provides a labeled transition metal complex comprising a transition metal atom, a reactive moiety for allowing a chemical or biological entity to become attached to the transition metal atom, an inert tridentate moiety as a stabilizing bridge, and a marker.

DETAILED DESCRIPTION

Figure 1:
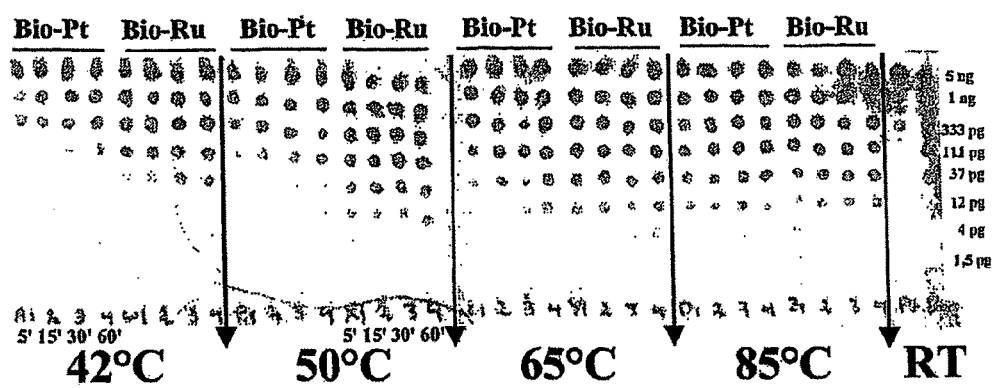
FIG. 1 depicts labelling of total human DNA (500-1500 bp) with Bio-BOC-Pt or Bio-APET-Ru. Incubation time and temperatures as DNA labelling parameters. Direct spotting of labelled DNA and detection with anti-Biotin-AP (NBT/BCIP).

Surprisingly, the present inventors have developed a novel category of transition metal complexes that can be labeled to a chemical or biological entity at least as efficient as the known methods. Further, it is conceived that nucleotides linked to the labeling system of the invention may be built in into polynucleotides very efficiently.

These labeled transition metal complexes comprise an inert tridentate moiety as stabilizing bridge, a marker, and a reactive moiety for allowing a chemical or biological entity to become attached to the transition metal atom.

Accordingly, the present invention relates to a labelled transition metal complex comprising a transition metal atom, a reactive moiety for allowing a chemical or biological entity to become attached to the transition metal atom, an inert tridentate moiety as a stabilizing bridge, and a marker.

These transition metal complexes can be prepared in higher yields than those which are based on bidentate moieties, whereas they display in addition improved stabilities and purities. Moreover, the present metal complexes are more reactive and bring about a more effective labelling when compared with transition metal complexes that are based on bidentate moieties. Furthermore, the preparation of a transition metal complex according to the invention can be carried out in a one-step procedure, which is highly advantageous.

Among the advantages of the use of tridentate ligands are the chelate effect and the trans effect. The chelate effect refers to the faster and more efficient coordination of a transition metal atom to the ligand due to the fact that the metal binds to three sites of one and the same molecule. As a result, the purity wherein the complex is obtained is higher. The trans effect refers to the increased reactivity and labelling efficiency of a transition metal complex according to the invention, due to the fact that the leaving groups is located in the trans position of a binding site of the tridentate moiety, imparting a polar character to the configuration. This binding site is preferably a secondary or tertiary amine, thereby contributing to said polar character.

Almost every chemical or biological entity which contains an accessible S (sulphur) atom or N (nitrogen) atom can be labeled with the labeled transition metal complexes according to the present invention. Suitable entities to be labeled with the labeled transition metal complexes are bio-organic molecules such as nucleic acid (nucleosides, nucleotides, oligonucleotides, DNA, RNA, homo duplexes, heteroduplexes, or multiplexes). The transition metal complexes bind very easily (non-covalently) to the N-7 position of guanine residues. This way DNA or RNA molecules, be it single stranded or otherwise can be easily identified (e.g. detected, separated, purified, isolated), but it also allows for the production of probes for hybridization techniques wherein unlabeled DNA/RNA molecules hybridize to the labeled probe. The labeled transition metal complexes do hardly interfere with the hybridization, if at all. Also, this technique obviates the use of modified nucleotides in preparing probes. However, proteins, peptides and other bio-organic molecules can also be identified with the labeling substances according to the invention.

The labeled transition metal complexes according to the present invention are also very suitable for attaching bio-organic molecules to solid surfaces such as nitrocellulose, nylon filters, microtiter plates, beads, glass, fibers and the like.

Nucleotides modified by using a transition metal complex according to the invention and oligo- and polynucleotides into which the nucleotides have been built in, or oligo- and polynucleotides that have been directly modified using these novel platinum compounds may be used as probes in bio-medical research, clinical diagnostics and recombinant DNA technology.

The wide variety of utilities of the complexes according to the invention are based upon the ability of the transition metal complexes to form stable complexes with bio-organic molecules, e.g. (poly)nucleic acids or (poly)peptides and derivatives thereof which in turn might be detected either by means of detectable moieties which are attached to or which interact with bio-organic molecules. Some uses include detecting and identifying nucleic acid containing etiological agents, e.g. bacteria and viruses; screening bacteria for antibiotic resistance; screening animals for genetic disorders in relation to pharmaceutical effects; diagnosing genetic disorders, e.g. trisomy 21, sickle cell anemia: chromosomal karyotyping; and identifying tumor cells. Furthermore, the labeling complexes are very useful in pharmacology, especially drug screening, drug target identification, drug monitoring and drug delivery.

The invention also encompasses a diagnostic kit for identifying, determining and/or localizing biological substances of interest, comprising the transition metal complex of the invention, optionally together with other suitable means for detection. Of course, the invention also encompasses a kit, wherein the respective components of the labeled transition metal complex are present separately, i.e. in unbound form.

Examples of suitable transition metal complexes in accordance with the present invention are complexes wherein the transition metal is chosen from the group consisting of vanadium, chromium, iron, nickel, copper, ruthenium, palladium, platinum, molybdenum, tungsten, cobalt, manganese, osmium, rhodium, iridium, zinc, and cadmium. Preferably, in accordance with the present invention the transition metal is chosen from the group consisting of iron, nickel, ruthenium, palladium, platinum, molybdenum, tungsten, and cobalt. More preferably, the transition metal is platinum, cobalt, or ruthenium.

The reactive moiety of the transition metal complex is suitably a good leaving ligand. Preferably, the reactive moiety is chosen from the group of $Cl^-$, $NO_3^-$, $HCO_3^-$, $CO_3^{2-}$, $SO_3^{2-}$, $ZSO_3^-$, $I^-$, $Br^-$, $F^-$, acetate, carboxylate, phosphate, ethyl nitrate, oxalate, citrate, a phosphonate, $ZO^-$, and water. Z is defined herein as a hydrogen moiety or an alkyl or aryl group having from 1 to 10 carbon atoms. Of these ligands, $Cl^-$ and $NO_3^-$ are most preferred.

The labeled transition metal complexes in accordance with the present invention comprise an inert tridentate as a stabilizing bridge. Inert as used herein indicates that the moiety remains attached to the transition complex during the labeling process and thereafter without chemically reacting with an entity.

The transition metal is attached to the tridentate moiety by means of nitrogen, oxygen, sulphur or phosphorus atoms that are present in the tridentate moiety, or any combination of these atoms. For example, the transition metal can be attached to the tridentate moiety by means of two nitrogen atoms and one oxygen atom or sulphur atom. Preferably, however, the transition metal is attached to the tridentate moiety by means of three nitrogen atoms.

In the context of the present invention, the hardness of a chemical element is defined as the ratio of the oxidation state and the radius of the atom. Based on this definition, hardness increases from left to right in a row of the Periodic Table, and decreases from top to bottom in a column of the Periodic Table. It is preferred that a transition metal is combined with a tridentate moiety that binds to the transition metal through an atom (nitrogen, oxygen, sulphur, or phosphorus) of similar hardness as that of the transition metal, since this has a beneficial effect on the stability of the resulting complex. Based on this approach, platinum is preferably combined with a tridentate moiety that binds to it through nitrogen or sulphur.

It is further preferred that the oxidation state of the transition metal is chosen such that a stable combination is achieved with a particular tridentate moiety. For instance, tridentate moieties binding to the transition metal through oxygen are preferably combined with Pt(IV), Pd(IV), Mo(VI), W(VI), Ru(III), Co(III), Fe(II), and Fe(III), rather than with Pt(II) or Pd(II). Tridentate moieties binding to the transition metal through nitrogen are considered to not have a particular preference for a particular oxidation state of the transition metal, although Cu(I) is less preferred. Tridentate moieties binding to the transition metal through phosphorus or sulphur are preferably combined with Pt(II), Pd(II), Fe(II), Co(II), rather than with Pt(IV), Fe(III), or Ru(III).

In general, suitable tridentate moieties that can be used in accordance with the present invention include those having at least three donor atoms independently chosen from N, P, S and O and separated by 1 to 5, preferably 1 to 3, atoms.

Preferred tridentate moieties that can be used in accordance with the present invention include those having the following formula, wherein said formula, due to the various possible combinations of X, Y and Z, gives rise to various embodiments, each having specific combinations of X, Y and Z, said individual embodiments herein being referred to as a "bloc":

 (I)

wherein for
Bloc I
X is NR or PR or O or S; R is one of H, a substituted or non-substituted aliphatic chain, a diene or non-diene, aromatic or non-aromatic, 5- or 6-membered, substituted or non-substituted ring linked to X via an atom of said chain or said ring but not via a hetero-atom; and Y and Z are independently chosen from the group of $(CH_2)_nNR_1R_2$, $(CH_2)_nPR_1R_2$, $R_3R_4C=NR_2$, $R_3R_4C=PR_2$, $(CH_2)_nC(O)R_2$, $(CH_2)_nC(O)NR_2R_3$, $(CH_2)_nC(O)PR_2R_3$, $(CH_2)_nC(O)N=R_2$, $(CH_2)_nC(O)P=R_2$, $(CH_2)_nC(O)OR_5$, $(CH_2)_nC(S)R_2$, $(CH_2)_nC(S)NR_2R_3$, $(CH_2)_nC(S)PR_2R_3$, $(CH_2)_nC(S)OR_5$, $(CH_2)_nC(S)N=R_2$, $(CH_2)_nC(S)P=R_2$, $R_6OR_5$, $R_6SR_2$, $R_7COO^-Na^+$, $R_7CSO^-Na^+$, $R_7CSS^-Na^+$, or $R_8-R_9$, wherein n is 1-5 and preferentially 1 to 3,
$R_1$ is one of H, $C(O)R_3$, $C(S)R_3$, a substituted or non-substituted aliphatic chain, a diene or non-diene, aromatic or non-aromatic, 5- or 6-membered, substituted or non-substituted ring linked to an N atom or to a P atom via said H, or said C, or an atom of chains or said ring, and $R_1$ is not bound to X. $R_2$ is one of H, a substituted or non-substituted aliphatic chain, a diene or non-diene, aromatic or non-aromatic, 5- or 6-membered, substituted or non-substituted ring linked to an N atom or a P atom via said H or an atom of said chain or said ring, or to C in C(O), $(CH_2)_nC(O)R_2$, $(CH_2)_nC(S)R_2$, and to C in $C(O)R_2$ and $C(S)R_2$ in $R_5$, when $R_5$ is $C(O)R_2$ and $C(S)R_2$, via an atom of said chain or said ring, or an hetero atom of a substituent of said chain or of a substituent of said ring in $R_2$, but not via any atom part of C(O) or C(S). $R_2$ is not bound to X. $R_3$ is one of H, a substituted or non-substituted aliphatic chain, a diene or non-diene, aromatic or non-aromatic, 5- or 6-membered, substituted or non-substituted ring linked to an N atom or to a P atom via said H or an atom of said chain or said ring, and to $R_1$ when $R_1$ is one of $C(O)R_3$ and $C(S)R_3$, via an atom of said chain or said ring or an atom of a substituent of said chain or of a substituent of said ring but not via any atom part of C(O) or C(S), $R_3$ is not bound to X. $R_4$ is one of H, a substituted or non-substituted aliphatic chain, a diene or non-diene, aromatic or non-aromatic, 5- or 6-membered, substituted or non-substituted ring linked to an C atom via said H or an atom of said chain or of said ring or an atom of a substituent of said chain or of a substituent of said ring. $R_4$ is not bound to X. $R_5$ is one of H, $C(O)R_2$, $C(S)R_2$, a substituted or non-substituted aliphatic chain, a diene or non-diene, aromatic or non-aromatic, 5- or 6-membered, substituted or non-substituted ring linked to an O atom via said H, or said C, or an atom of said chain or of said ring. $R_5$ is not bound to X. $R_6$ is a substituted or non-substituted aliphatic chain, the number of carbon atoms between X and O in $R_6OR_7$, and between X and S in $R_6SR_2$ varying between 1 and 5 and is preferentially 2 or 3. $R_6$ is bound to X via a $CH_2$ group. $R_7$ is one of a substituted or non-substituted aliphatic chain, a diene or non-diene, aromatic or non-aromatic, 5- or 6-membered, substituted or non-substituted ring with the number of carbon atoms between X and one of the O atoms in $COO^-$ or in $R_7COO^-Na^+$, between X and the S atom in $COS^-$ in $R_7COS^-Na^+$, and between X and one of the S atoms in $CSS^-$ in $R_7CSS^-Na^+$ varying between 1 and 5 and is preferentially 2 or 3. $R_7$ is not bound to X. $R_8$ is a substituted or non-substituted aliphatic chain with the number of carbon atoms between X and the atom connecting $R_8$ to $R_9$ varying between 1 and 5, preferentially 2 or 3. $R_9$ is a substituted or non-substituted, 5 or 6-membered, N— and/or P— and/or O— and/or S— containing, a diene or non-diene, aromatic or non-aromatic, 5- or 6-membered, substituted or non-substituted ring with the number of atoms between X and the co-ordinating atom in the ring varying between 2 and 10 and is preferentially 2 or 3. $R_9$ is not bound to X.
Bloc II
Y and Z are the same, and X, Y and Z are independently a substituted or non-substituted, 5 or 6-membered, N— and/or P and/or O— and/or S— containing, diene or non-diene containing, aromatic or non-aromatic ring with the number of atoms between the co-ordinating atoms of X and both Y and Z being 1 to 5, preferably 2 or 3;
Bloc III
X is NR or PR or O or S; R is one of H, a substituted or non-substituted aliphatic chain, a diene or non-diene, aromatic or non-aromatic, 5- or 6-membered, substituted or non-substituted ring linked to X via an atom of said chain or said ring but not via a hetereo-atom; Z is chosen from the group of H, $(CH_2)_nNR_1R_2$, $(CH_2)_nPR_1R_2$, $R_3R_4C=NR_2$, $R_3R_4C=PR_2$, $(CH_2)_nC(O)R_2$, $(CH_2)_nC(O)NR_2R_3$, $(CH_2)_nC(O)PR_2R_3$, $(CH_2)_nC(O)N=R_2$, $(CH_2)_nC(O)P=R_2$, $(CH_2)_nC(O)OR_5$, $(CH_2)_nC(S)R_2$, $(CH_2)_nC(S)NR_2R_3$, $(CH_2)_nC(S)PR_2R_3$, $(CH_2)_nC(S)OR_5$, $(CH_2)_nC(S)N=R_2$, $(CH_2)_nC(S)P=R_2$, $R_6SR_2$, $R_7COO^-Na^+$, $R_7CSO^-Na^+$, $R_7CSS^-Na^+$, $R_8-R_9$ as defined hereinbefore (bloc I); and Y is $A_2N(C_2H_4)NA(C_2H_4)$ or $A_2N(C_2H_4)NA(C_2H_4)$ or $A_2P(C_2H_4)NA(C_2H_4)$ or $A_2N(C_2H_4)PA(C_2H_4)$ or $A_2P(C_2H_4)PA(C_2H_4)$, wherein A has the same meaning as Z;
Bloc IV
X is NR or PR or O or S; R is one of H, a substituted or non-substituted aliphatic chain, a diene or non-diene, aromatic or non-aromatic, 5- or 6-membered, substituted or non-substituted ring linked to X via an atom of said chain or said ring but not via a hetereo-atom; Z is chosen from the group of H, $(CH_2)_nNR_1R_2$, $(CH_2)_nPR_1R_2$, $R_3R_4C=NR_2$, $R_3R_4C=PR_2$, $(CH_2)_nC(O)R_2$, $(CH_2)_nC(O)NR_2R_3$, $(CH_2)_nC(O)PR_2R_3$, $(CH_2)_nC(O)N=R_2$, $(CH_2)_nC(O)P=R_2$, $(CH_2)_nC(O)OR_5$, $(CH_2)_nC(S)R_2$, $(CH_2)_nC(S)NR_2R_3$, $(CH_2)_nC(S)PR_2R_3$, $(CH_2)_nC(S)OR_5$, $(CH_2)_nC(S)N=R_2$, $(CH_2)_nC(S)P=R_2$, $R_6OR_5$, $R_6SR_2$, $R_7COO^-Na^+$, $R_7CSO^-Na^+$, $R_7CSS^-Na^+$, and $R_8-R_9$ as defined hereinbefore (bloc I); and Y is $R_2R_3NC(O)CH_2N(C_2H_4)R_{10}$, $R_2R_3PC(O)CH_2N(C_2H_4)R_{10}$, $R_5OC(O)CH_2N(C_2H_4)R_1$, $R_1R_2NC(O)CH_2O(C_2H_4)$, $R_1R_2PC(O)CH_2O(C_2H_4)$, $R_5OC(O)CH_2O(C_2H_4)$, $R_1R_2NC(O)CH_2S(C_2H_4)$, $R_1R_2PC(O)CH_2S(C_2H_4)$, $R_5OC(O)CH_2S(C_2H_4)$, $R_2R_3NC(O)CH_2P(C_2H_4)R_{10}$, $R_2R_3PC(O)CH_2P(C_2H_4)R_{10}$, $R_5OC(O)CH_2P(C_2H_4)R_1$, $R_1R_2NCH_2C(O)N(C_2H_4)R_{10}$, $R_1R_2PCH_2C(O)N(C_2H_4)R_{10}$, $R_5OCH_2C(O)N(C_2H_4)R_2$, $R_2SCH_2C(O)N(C_2H_4)R_{10}$, $R_1R_2NCH_2C(O)O(C_2H_4)$, $R_1R_2PCH_2C(O)O(C_2H_4)$, $R_5OCH_2C(O)O(C_2H_4)$, $R_2SCH_2C(O)O(C_2H_4)$, $R_1R_2NCH_2C(O)P(C_2H_4)R_{10}$, $R_1R_2PCH_2C(O)P(C_2H_4)R_{10}$, $R_5OCH_2C(O)P(C_2H_4)R_2$, $R_2SCH_2C(O)P(C_2H_4)R10$, $R_1R_2N(CH_2)nO(CH_2)nC(O)$, $R_1R_2P(CH_2)nO(CH_2)nC(O)$, $R_5O(CH_2)nO(CH_2)nC(O)$, $R_2S(CH_2)nO(CH_2)nC(O)$, $R_1R_2N(CH_2)nS(CH_2)nC(O)$, $R_1R_2P(CH_2)nS(CH_2)nC(O)$, $R_5O(CH_2)nS(CH_2)nC(O)$, $R_2S(CH_2)nS(CH_2)nC(O)$, $R_1R_2N(CH_2)nO(CH_2)n$, $R_1R_2P(CH_2)nO(CH_2)n$, $R_5O(CH_2)nO(CH_2)n$, $R_2S(CH_2)nO(CH_2)n$, $R_1R_2N(CH_2)nS(CH_2)n$, $R_1R_2P(CH_2)nS(CH_2)n$, $R_5O(CH_2)nS(CH_2)n$, $R_2S(CH_2)nS(CH_2)n$, $R_1R_2N(CH_2)n(NR_3)(CH_2)nC(O)$, $R_1R_2P(CH_2)n(NR_3)(CH_2)nC(O)$, $R_5O(CH_2)n(NR_3)(CH_2)nC(O)$, $R_2S(CH_2)n(NR_3)(CH_2)nC(O)$, $R_1R_2N(CH_2)n(NR_3)(CH_2)nC(O)$, $R_1R_2P(CH_2)n(NR_3)(CH_2)nC(O)$, $R_5O$ $(CH_2)n(NR_3)(CH_2)nC(O)$, $R_2S(CH_2)n(NR_3)(CH_2)nC(O)$, $R_1R_2N(CH_2)nN(CH_2)nR_3$, $R_1R_2P(CH_2)nN(CH_2)nR_3$, $R_5O(CH_2)nN(CH_2)nR_3$, $R_2S(CH_2)nN(CH_2)nR_1$, $R_1R_2N(CH_2)nN(CH_2)nR_3$, $R_1R_2P(CH_2)nN(CH_2)nR_3$, $R_5O(CH_2)nN(CH_2)nR_1$, $R_2S(CH_2)nN(CH_2)nR_1$, $R_1R_2N(CH_2)n(PR_3)(CH_2)nC(O)$, $R_1R_2P(CH_2)n(PR_3)(CH_2)nC(O)$, $R_5O(CH_2)n(PR_3)(CH_2)nC(O)$, $R_2S(CH_2)n(PR_3)(CH_2)nC(O)$, $R_1R_2N(CH_2)n(PR_3)(CH_2)nC(O)$, $R_1R_2P(CH_2)n(PR_3)(CH_2)nC(O)$, $R_5O(CH_2)n(PR_3)(CH_2)nC(O)$, $R_2S(CH_2)n(PR_3)(CH_2)nC(O)$, $R_1R_2N(CH_2)nP(CH_2)nR_3$, $R_1R_2P(CH_2)nP(CH_2)nR_3$, $R_5O(CH_2)nP(CH_2)nR_1$, $R_2S(CH_2)nP(CH_2)nR_1$, $R_1R_2N(CH_2)nP(CH_2)nR_3$, $R_1R_2P(CH_2)nP(CH_2)nR_3$, $R_5O(CH_2)nP(CH_2)nR_1$, and $R_2S(CH_2)nP(CH_2)nR_1$. Within Y, $R_1$ through $R_5$ all have the same meaning as in bloc I except for $R_1$ and $R_3$. $R_1$ is one of H, $C(O)R_{11}$, $C(S)R_{11}$, a substituted or non-substituted aliphatic chain, a diene or non-diene, aromatic or non-aromatic, 5- or 6-membered, substituted or non-substituted ring linked to an N atom or to a P atom via said H, or said C, or an atom of chains or said ring, and $R_1$ is not bound to X. $R_3$ is one of H, a substituted or non-substituted aliphatic chain, a diene or non-diene, aromatic or non-aromatic, 5- or 6-membered, substituted or non-substituted ring linked to an N atom or to a P atom via said H or an atom of said chain or said ring via an atom of said chain or said ring or an atom of a substituent of said chain or of a substituent of said ring, $R_3$ is not bound to X. $R_{10}$ is one of H, $C(O)R_{12}$, $C(S)R_{12}$, a substituted or non-substituted aliphatic chain, a diene or non-diene, aromatic or non-aromatic, 5- or 6-membered, substituted or non-substituted ring linked to an N atom or to a P atom via said H, or said C, or an atom of chains or said ring, and $R_{10}$ is not bound to X. $R_{11}$ is one of H, a substituted or non-substituted aliphatic chain, a diene or non-diene, aromatic or non-aromatic, 5- or 6-membered, substituted or non-substituted ring linked to C in $R_1$ when $R_1$ is $C(O)R_{11}$ or $C(S)R_{11}$ via an atom of said chain or said ring via an atom of a substituent of said chain or of a substituent of said ring but not via any atom of C(O) or C(S). $R_{11}$ is not bound to X. $R_{12}$ is one of H, a substituted or non-substituted aliphatic chain, a diene or non-diene, aromatic or non-aromatic, 5- or 6-membered, substituted or non-substituted ring linked to C in $R_{10}$ when $R_{10}$ is $C(O)R_{12}$ or $C(S)R_{12}$ via an atom of said chain or said ring via an atom of a substituent of said chain or of a substituent of said ring but not via any atom of C(O) or C(S). $R_{12}$ is not bound to X.

Bloc V

X is NR or PR or O or S; R is one of H, a substituted or non-substituted aliphatic chain, a diene or non-diene, aromatic or non-aromatic, 5- or 6-membered, substituted or non-substituted ring linked to X via an atom of said chain or said ring but not via a hetero-atom; and Y and Z are independently $ABN(CH_2)_n$, $ABP(CH_2)_n$ wherein n is 2 or 3, and A and B are chosen from the group of $(CH_2)_nNR_1R_2$, $(CH_2)_nPR_1R_2$, $R_3R_4C=NR_2$, $R_3R_4C=PR_2$, $(CH_2)_nC(O)R_2$, $(CH_2)_nC(O)NR_2R_3$, $(CH_2)_nC(O)PR_2R_3$, $(CH_2)_nC(O)N=R_2$, $(CH_2)_nC(O)P=R_2$, $(CH_2)_nC(O)OR_5$, $(CH_2)_nC(S)R_2$, $(CH_2)_nC(S)NR_2R_3$, $(CH_2)_nC(S)PR_2R_3$, $(CH_2)_nC(S)OR_5$, $(CH_2)_nC(S)N=R_2$, $(CH_2)_nC(S)P=R_2$, $R_6OR_5$, $R_6SR_2$, $R_7COO^-Na^+$, $R_7CSO^-Na^+$, $R_7CSS^-Na^+$, or $R_8$-$R_9$, wherein n is 1-5 and preferentially 2 or 3, as defined hereinbefore (bloc I).

Bloc VI

Any substituted macrocycle containing a minimum of three hetero-atoms independently chosen from N—, P—, O— and S—. A macrocycle is defined as a cyclic molecule containing a minimum of nine atoms of which three or more are donor hetero-atoms Bloc VII X is a substituted or non-substituted, 5 or 6-membered, N— and/or P and/or O— and/or S— containing, diene or non-diene, aromatic or non-aromatic ring. At least one of Y or Z contains N—, and/or P—, and O—, and/or S— hetero-donor atoms and is a substituted or non-substituted aliphatic chain, or a a diene or non-diene, aromatic or non-aromatic, 5- or 6-membered, substituted ring attached to X via this substituent on the ring. If only one of Y or Z contains N—, and/or P—, and/or O—, and/or S— hetero-donor atoms, then the candidate between Y and Z satisfying this criteria contains a minimum of two N—, and/or P—, and/or O—, and/or S— hetero-donor atoms the number of atoms between these two hetero-donor atoms and also between the closest of these hetero-atoms to X and the closest hetero-donor atom in X, being of 2 or 3. If both Y and Z contain hetero-donor atoms, then Y and Z each contain a minimum of one N— or P— or O— or S— hetero-donor atom, the number of atoms between the hetero-donor atom of Y and the hetero-donor atom of X, and between the hetero-donor atom of Z and the hetero-donor atom of X being of 2 or 3.

Furthermore, preferred tridentate moieties that can be used in accordance with the present invention include those having the following formula:

$$YXZ \qquad (II)$$

wherein:

X, Y and Z are independently a substituted or non-substituted, 5 or 6-membered, N— and/or P and/or O— and/or S— containing, diene or non-diene containing, aromatic or non-aromatic ring with the number of atoms between the co-ordinating atoms of X and both Y and Z being 1.

In principle, any type of nitrogen, oxygen, phosphorus, or sulphur containing reactive site of an entity may be labeled using a method according to the invention. Preferred reactive sites include reactive sites comprising an amine, a phosphoamine, a thiol, a thioether, a sulfide, a thioamide, a thiol, an amide, a phosphoamide, a thiophosphamide, an imide, an imine, a phosphoimine, an aldehyde, a ketone, an ester, an anhydride, a thianhydride, an alcohol, an ether, an urea, a thiourea, a phosphourea, an acylurea, an acylphosphourea, an oxourea, a thioaldehyde, a thioketone, a thioester, a thiophosphate, a thioanhydride, a carboxylic acid or thiocarboxylic acid and salts thereof, or a pyridine, an imidazole, a pyrazole, a phosphopyridine, a phosphoimidazole, a phosphopyrazole, a furane, or a thiophene. Examples of entities that can be labeled are entities chosen from the group of amino acids (preferably methionine, cysteine, and histidine), peptides, oligopeptides, polypeptides, proteins, immunoglobulins, enzymes, synzymes, phospho-amino acids, phospholipides lipids (e.g. phosphatidyl choline, sphingolipids), glycoproteins, nucleic acids, nucleosides, nucleotides, oligonucleotides, polynucleotides, peptide nucleic acids, peptide nucleic acid oligomers, peptide nucleic acid polymers, amines, aminoglycosides, nucleopeptides, and glycopeptides. Preferably in accordance with the invention, the entity is chosen from the group of nucleic acids, nucleosides, nucleotides, oligonucleotides, polynucleotides, amino acids, peptides, oligopeptides and polypeptides.

In accordance with the present invention the marker is suitably contained in the inert tridentate moiety or attached to the tridentate moiety, optionally by means of a spacer. In case the oxidation state of the transition metal is higher than (II), the marker can also be attached to the transition metal.

Any type of marker may be used as long as it can be contained in the inert moiety or attached to the spacer which is in turn attached to the tridentate moiety. Such a marker may be a radioactive label; an enzyme; a specific binding pair component such as avidin, streptavidin or biotin, biocytin, iminobiotin; a colloidal dye substance; a phosphorescent label (e.g. a europium chelate, a platinum porphyrine); a chemiluminescent label (e.g. luminol); a fluorochrome, including a cyanine, a Alexa dye (Molecular Probes), or Bodipy-colourant (Molecular Probes), a rhodamine, carboxyrhodamine; dinitrophenol (DNP); tert-butoxycarbonyl; a lanthanide, e.g. Europium or Terbium whether or not in a chelate configuration; a reducing substance (eosin, erythrosin, etc.); a (coloured) latex sol; digoxigenin; a metal (e.g. ruthenium, for instance in case of bi- or polynuclear complexes); a metal sol or another particulate sol (selenium, carbon and the like); dansyl lysine; a UV dye; a VIS dye; Infra Red dye; coumarine (e.g. amino methyl coumarine); a solid support; a nucleoside, a nucleotide, a oligo- or polynucleotide, an antibody, an amino acid, a protein or (poly)peptide having a physiological effect on or in a cell (e.g. protein A, protein G, membrane shuttle molecule), etc. A special class of marker is the transition metal itself. Said transition metal marker can be present without any other transition metal marker (mononuclear) or combined with other transition metal markers (bi- or polynuclear) in both homo or hetero configuration, or whether or not combined with other types of markers as described above. Those labeling complexes are especially useful in electrochemical detection means, e.g. biosensors.

Particular preferred are DNP, fluorescein, cyanine-colorants and tetramethylrhodamine, inter alia because they can form stable complexes with platinum linked to an entity. Other preferred markers include biotin, avidin, streptavidin and digoxygenin.

In one embodiment of the present invention the marker is connected to the inert tridentate moiety by means of a spacer. Preferably such a spacer comprises a chain having at least four atoms, and preferably not more than 20 atoms, which chain comprises an electron donating moiety on one end and a moiety for reacting with the marker, wherein the chain is attached to the tridentate moiety through the electron donating moiety. It is possible to attach first the spacer to the marker before the spacer reacts with the tridentate moiety. The electron donating moiety of the spacer may for example be an amine group or a thiolate anion. Preferably the chain further comprises at least one hetero-atom. Highly preferred spacers are polyethylene glycol, 1,6-diaminohexane and 1,8-diamino-3,6-dioxaoctane. In a preferred embodiment of the invention use is made of 1,6-diaminohexane tert-butoxycarbonyl, as an intermediate transition metal-spacer complex, prior to attaching to the marker. In preferred embodiments the spacers differ in molecular mass by substituting atoms, e.g. with alternative isotopes.

Figure 6:
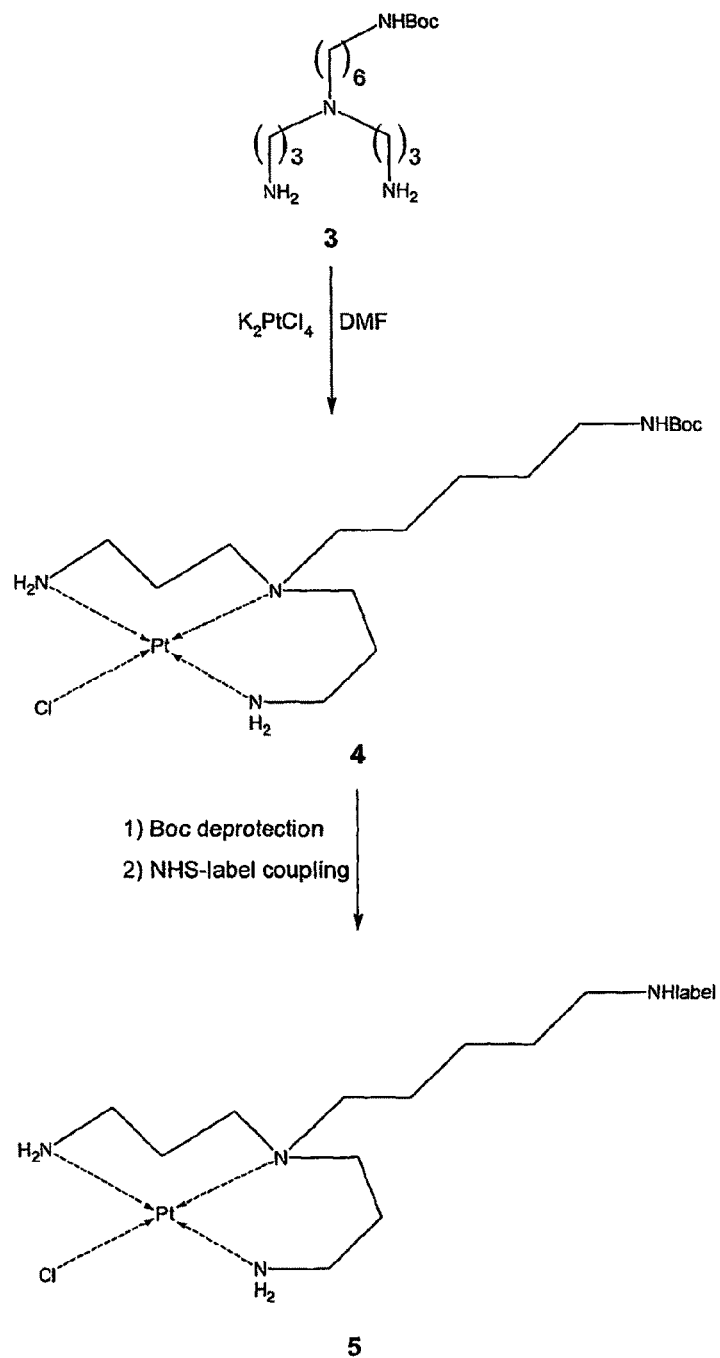
FIG. 6 depicts route to labeled Pt(II) complexes from compound 3.
Figure 8:
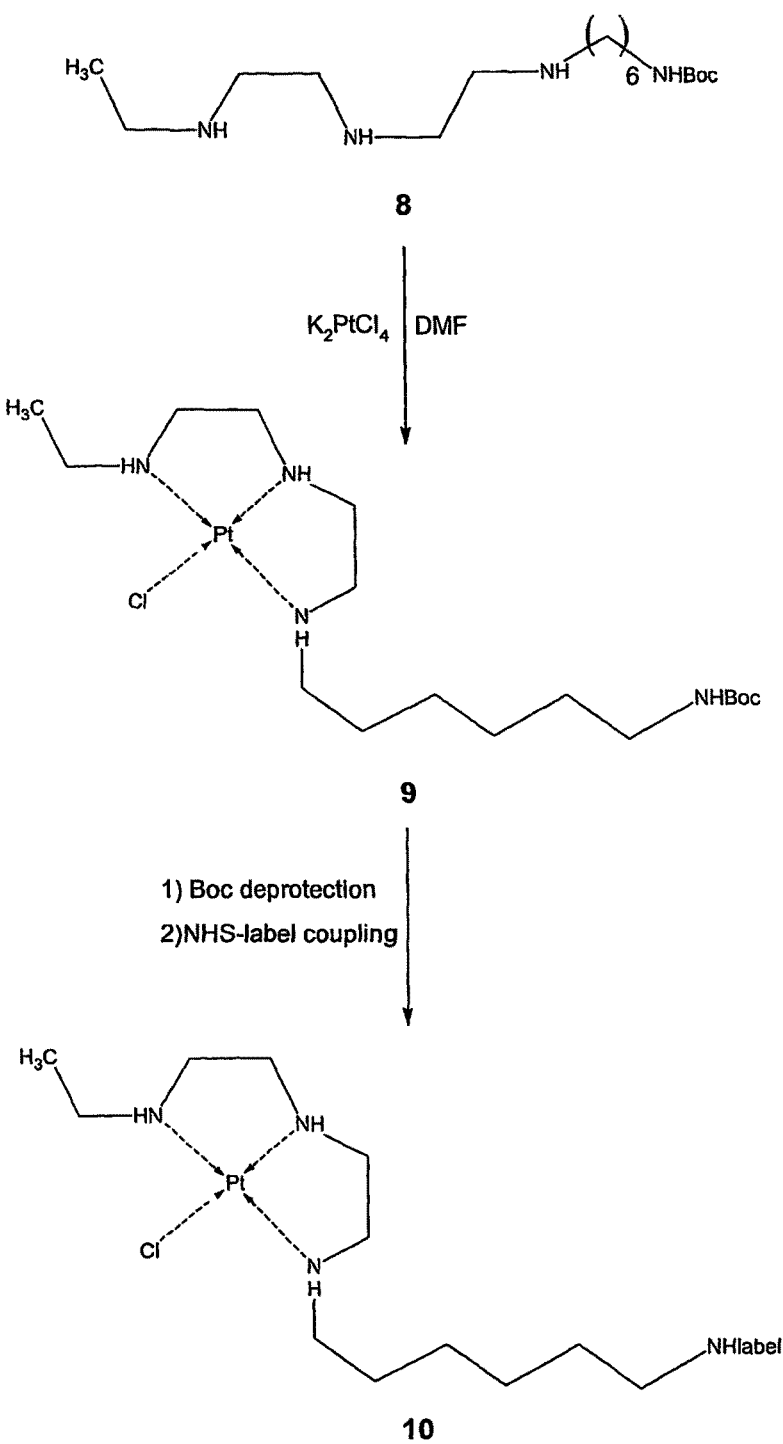
FIG. 8 depicts route to labeled Pt(II) complexes from compound 8.
Figure 9:
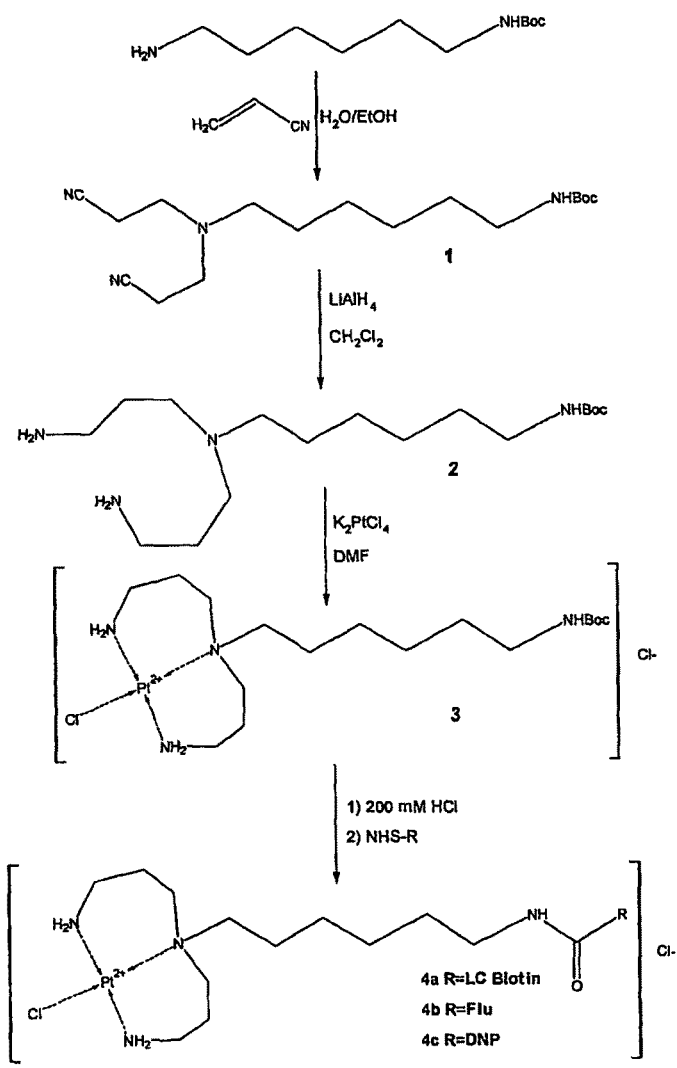
FIG. 9 depicts synthesis of $N_3$ trans-C3 tridentate.
Figure 13:
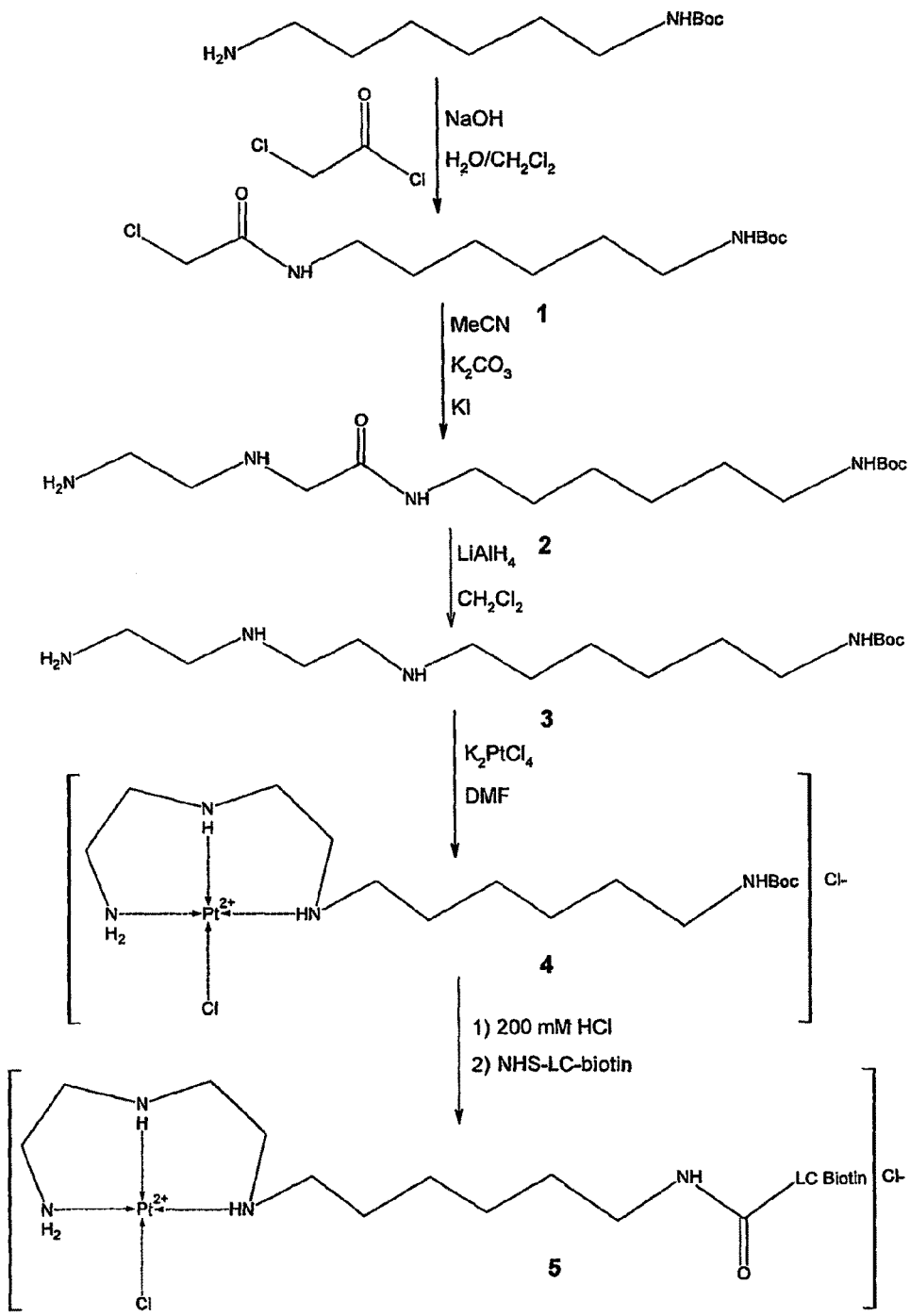
FIG. 13 depicts synthesis of the $N_3$ cis-C2 tridentate.
Figure 16:
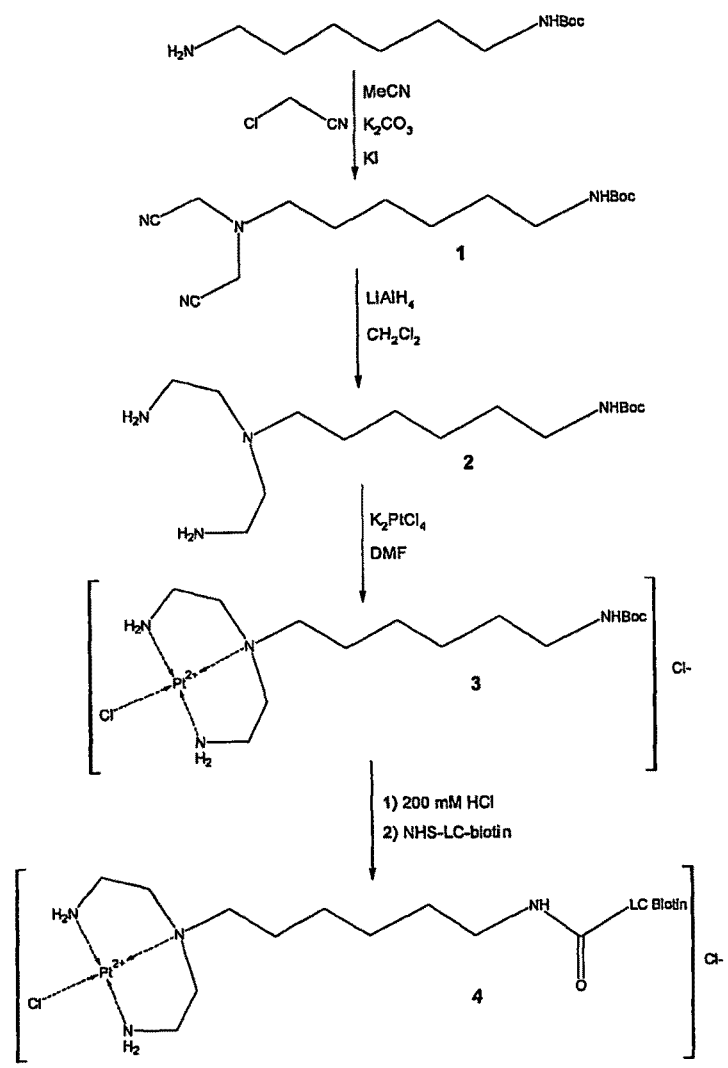
FIG. 16 depicts synthesis of the $N_3$ trans-C2 tridentate.
Figure 17:
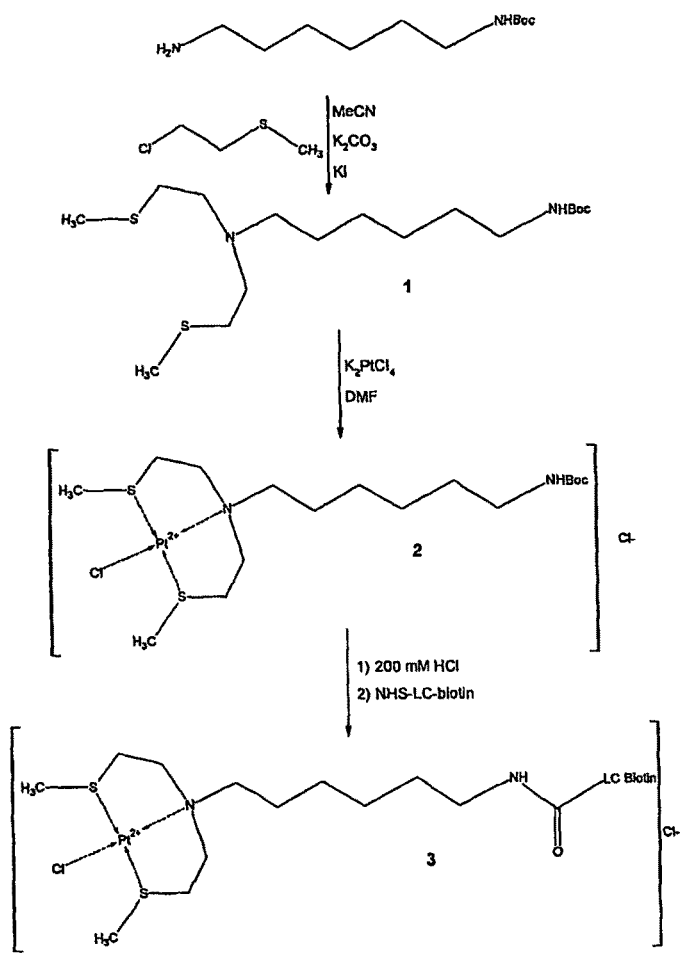
FIG. 17 depicts synthesis of the $NS_2$ trans-C2 tridentate.

Particularly preferred complexes of the present invention are the tridentate moiety-comprising transition metal complexes as described in the appending Examples. Specific reference is made to preferred embodiments therein referred to as an $N_a$ trans-C3 tridentate complex, such as for instance shown in FIG. 6, compound no. 5, and FIG. 9, compound 4; an $N_3$ cis-C2 tridentate complex such as for instance shown in FIG. 8, compound no. 10, and FIG. 13, compound no. 5; an $N_3$ trans-C2 tridentate complex such as for instance shown in FIG. 16, compound no. 4; an $NS_2$ trans-C2 tridentate complex such as for instance shown in FIG. 17, compound no. 3; a bridged (pyridine)$_3$ trans tridentate complex such as for instance shown in FIG. 15 compound 7. The term "cis" herein refers to the position of the leaving group and the marker (optionally linked via a spacer arm) on the transition metal being adjacent, while the term "trans" herein refers to the position of the leaving group and the marker (optionally linked via a spacer arm) on the transition metal being opposite. The indication C2 or C3 indicates the size in number of carbon atoms that bridge the individual teeth, while $N_3$ indicates that the tridentate teeth are all nitrogen atoms, $NS_2$ indicates that two of the tridentate teeth are sulphur atoms, the third being a nitrogen atom. The term "tridentate teeth" herein referring to the part of the tridentate moiety actually participating in the coordination bonding to the transition metal.

The particular advantage of the complex of the present invention is that it allows for the possibility of coordinated bond formation between the transition metal complex and the chemical or biological entity thereby greatly enhancing its suitability for use as a labeling compound. This labeling compound preferably comprises as a marker moiety a fluorescent label, such as fluorescein; amino-methyl coumarin (AMCA); tetramethyl rhodamine (TAMRA); diethyl aminomethyl coumarin (DEAC); Carboxy-Fluorescein (FAM); Carboxy-Tetra methylrhodamine (TAMRA); Carboxy-X-Rhodamine (ROX); Cascade Blue (CB); fluorescein isothiocyanate (FITC); Oregon Green (OG); Alexa 488 (A488); Rhodamine green (RGr); Carboxy-rhodamine 6G (R6G); Texas Red (TxR); Cy3; Cy3.5; Cy5, Cy5.5; Cy7, carboxynaphtofluorescein (CNF) and Bodipy® dyes, or a hapten label such as biotin (BIO); digoxigenin (DIG); and 2,4-dinitrophenyl (DNP). The transition metal complex of the present invention may therefore suitably be referred to as a labeling compound in its entirety. The labeling compound may very suitably be used to label nucleic acids. It will be appreciated that other chemical or biological entities, such as proteinaceous molecules may also be very suitably labeled by the tridentate complex of the present invention.

The invention further relates to a chemical or biological entity labeled with the labeled transition metal complex comprising at least one different stable isotope. Preferably, said entity is an amino acid, peptide or protein.

A particular aspect of the present invention relates to the use of the labeled transition metal complexes according to the invention in the identification of proteins and the mapping of their cellular interactions, which are important tools to understand the functioning of biological systems, and to evaluate the effect of disease states or drug administration. In that way, the composition of the proteome as well as qualitative and quantitative changes therein can be determined. The human proteome comprises more than 100 000 proteins with widely diverse characteristics, naturally occurring at concentration levels covering up to nine orders of magnitude. These figures illustrate some of the challenges faced by proteome researchers. The large-scale (ultimately global) analysis of proteins expressed in a cell or tissue has been termed proteome analysis (Pennington et al., 1997, Trends Cell Bio 7:168-173) or proteomics. Compared to genome analysis, proteome analysis is facing specific challenges.

A broad range of technologies is available to identify proteins and map their cellular interactions. In order to unravel the nature of an unknown protein and to assess its function, a number of subsequent steps is generally involved (Patterson and Aebersold, 2003, Nat. Genet. 33 Suppl:311-23).

A first step is formed by proteome display and mapping technologies. The most widely used procedure to obtain protein maps or fingerprints is two-dimensional gel electrophoresis (2DE) (Rabilloud, 2000, Anal Chem. 72(1):48A-55A). In 2DE, proteins are separated by their isoelectric point (pI) in one dimension followed by molecular weight (MW) separation in the second dimension. The separated proteins can be visualized using general stains such as Coomassie blue, silver stains, fluorescent dyes, or radio labeling (Patton, 2002, J Chromatogr B Analyt Technol Biomed Life Sci. 771 (1-2):3-31). The generated complex patterns of spots require advanced image analysis for further processing. Usually two or multiple protein profiles, representing e.g. different cell stages, are compared. Differentially expressed protein spots of interest are excised from gel for post-separation analysis. In this way the changes in the proteome due to an alteration in the cell's state can be visualized and the characteristic changes in protein expression can be pinpointed.

A subsequent second step is represented by protein identification technologies, predominantly Mass Spectrometry (MS). A mass spectrometer is essentially a combination of an ionization module, a mass analyzer and a detector and measures the mass-to-charge (m/z) ratio of ionized analytes (e.g. peptides or proteins). The analytes can be charged either by fast atom bombardment (FAB), electron spray ionization (ESI), matrix-assisted laser desorption ionization (MALDI) or atmospheric pressure chemical ionization (APcI). The mass analyzer is the most flexible part of the mass spectrometer. Since an electric field will deflect charged particles, and the energy potential can be converted to inertial movement based on the mass and the potential, the mass analyzer steers certain masses to the detector based on their mass-overcharge ratios (m/z) by varying the electrical field potentials. The analyzer can be used to stabilize a narrow range of m/z or to scan through a range of m/z to catalog the ions present. Several types exist, include time-of-flight, ion trap, and quadrupole mass analyzers. The detector simply records the charge induced when an ion passes by or hits a surface.

Because a mass spectrometer is a non-specific detector, specific interfaces are often used to link a mass spectrometer to a gas (GC) or liquid chromatograph (LC) for feeding separate analytes to the MS. A tandem mass spectrometer (MS-MS or MS$^n$) is one that is capable of multiple rounds of mass spectrometry. For example, one mass analyzer can isolate one peptide from many entering a mass spectrometer. A second mass analyzer then stabilizes the peptide ions while gas collides with them, causing them to fragment. A third mass analyzer then catalogs the fragments produced from the peptides. This process, called collision induced dissociation, is the basis of many experiments in proteomics. To date, various mass spectrometers are available, each featuring its specific advantages for certain applications (Gygi and Aebersold, 2000, Curr Opin Chem Biol. 4(5):489-94; Mann et al., 2001, Ann. Rev. Biochem. 70:437-473).

A final step in assessing the functional analysis of a proteins involves technologies such as surface plasmon resonance (SPR), which can provide detailed information on biomolecular interactions, e.g. of known proteins and their targets. The phenomenon of SPR occurs in a thin metal film at an optical interface under conditions of total reflection of polarized light at a specific angle. The procedure measures subtle changes in optical resonance, and is sensitive to the refractive index of the medium on the opposite side of this film. Changes in refractive index occur when molecules bind to, or dissociate from a biomolecule that has been attached to the metal surface. In this way, real time binding activity profiles are generated with association or dissociation characteristics of the interaction (Green et al., 2000, Biomaterials 21(18):1823-35; Rich and Myszka, 2000, Curr Opin Biotechnol. 11(1):54-61; McDonnell, 2001, Curr Opin Chem Biol. 5(5):572-7).

Technological advancements have generally been aimed at improving the sensitivity and quantification of detection of the various proteins. Moreover they have been aimed at providing methods that can make 2DE obsolete, i.e. to become gel-independent. The complexity of 2DE patterns and the inherent biases against low abundant, small (less than 10 kDa) or poorly soluble (e.g. membrane bound) proteins have triggered the development of techniques that allow (semi) quantitative measurements of proteins in a proteome directly (Regnier et al., 2002, J Mass Spectrom. 37(2):133-45; Bauer and Kuster, 2003, Eur J Biochem. 270(4):570-8).

A very suitable approach that circumvents the use of 2DE is the ICAT (isotope-coded affinity tags) procedure developed by Gygi et al. in 1999 (Nat. Biotechnol. 17(10):994-9). This procedure is capable of rapidly comparing two different global protein expression profiles by MS based on differential labeling with stable isotopes. The first generation ICAT reagent consisted of i) a thiol-specific protein reactive group (iodoacetamide) capable of labeling cysteine (Cys) residues of proteins, ii) two different linker moieties containing either eight hydrogen ($^1$H) atoms (d0, light isotope) or eight deuterium ($^2$H) atoms (d8, heavy isotope) for differential labeling of two populations of proteins, and iii) an affinity tag, mostly biotin, that enables selective isolation of labeled peptides.

The ICAT procedure itself involves the reduction and alkylation of the cysteine side chains in a complex mixture of proteins, whereby the proteins of one cell state are labeled with the d0-labeled tag and the proteins of a second cell state (e.g. a disease state) are labeled with the d8 form of the tag. The two mixtures are then combined and subjected to proteolytic digestion, in order to provide fragments amenable to MS analysis. The resultant complex mixture of proteolytic peptides is purified by affinity column chromatography to pull out the labeled sub-set of peptides. The sample is then analyzed by a combination of LC-MS, for providing the quantitative information or the abundance of proteins based on the relative abundance of the d0 and d8 isotopes, and LC-MS-MS, for providing the qualitative information based on the molecular mass of the peptide and the amino acid sequence information.

Improper co-elution of peptides labeled with the heavy ICAT reagent versus peptides labeled with the light ICAT, and poor recovery of affinity tag captured labeled peptides led to the development of the second generation ICAT reagent. These ICAT reagents are composed of i) a thiol-specific protein reactive group (iodoacetamide) capable of labeling cysteine (Cys) residues of proteins, ii) a linker moiety containing a defined number of either carbon atoms (light) or carbon isotopes (heavy) for differential labeling of two populations of proteins, an affinity tag, mostly biotin, that enables selective isolation of labeled peptides, and iv) acid cleavable site which allows removal of the biotin portion of the ICAT reagent tag prior to MS and MS-MS analysis. The protein reactive group covalently links the isotope-coded affinity tag to the protein by alkylation of free cysteines. Because the ICAT technique is based on labeling of the cysteine residue(s) of a protein, proteins that do not contain a cysteine will not be detected with ICAT. Moreover, the cysteine residue must be located in a tractable peptide; that is, a peptide that results from the proteolytic digestion with a molecular weight (MW) of approximately between 600 and 3500 Da. Peptides outside of this MW range will either not contain a sufficient number of amino acids to provide the necessary qualitative information for protein identification, or will be so large as to not be amenable to MS-MS fragmentation by collisionally activated dissociation. Moreover, the cysteine-based ICAT tags would not yield information on changes in the proteome based on post-translational modification such as phosphorylation, unless the modification fortuitously occurred in the cys-containing peptide.

Various alternative methods have been developed to differentially label proteins by both chemical and metabolic labeling procedures (Goshe and Smith, 2003, Curr Opin Biotechnol. 14(1):101-9). The chemical methods are based on classical protein modifications of individual peptides or protein trypsin digests. For instance, lysine (Lys) residues may be labeled at the C-terminus by using a heavy derivative of 2-methyloxy-1H-imidazole containing four $^2$H atoms (d4) (Peters et al., 2001, Rapid Commun Mass Spectrom. 15(24): 2387-92). Lys residues may also be labeled by differential guanidination using O-methyl-isourea in a process termed mass-coded abundance tagging (MCAT; Cagney and Emil. 2002. Nat Biotechnol. 20(2):163-70). Methionine (Met) residues may for instance be labeled by using activated esters of (d0/d4)-nicotinic acid (Shen et al., 2003. Molec Cell Proteomics 2:315-324). Cys residues may be labeled by differential alkylation using N-(d0/d5)-ethyl-iodoacetamide. Primary amines of peptides can be differentially labeled using N-acetoxy-(d0/d3)-succinimide derivatives (Chakraborty and Regnier, 2002).

In general, however, the above labeling methods require 2DE separation or—in the case of ICAT—affinity chromatography purification, to reduce the complexity of the mixtures before MS analysis. iTRAQ and iPROT are isobaric labelling technologies that do not use isotopes for differential screening but different isomers of a labelling reagent.

Also, the labeling chemistry involved lacks robustness, partly due to the instability of the chemical reagent and its undesired cross-reacting properties, which leads to heterogeneity in the signal pairs obtained. Also, the average human proteome coverage is relatively low, e.g. only ≈85% for ICAT. These factors hamper the utilization of differential labeling methods in proteome research, especially in case of (automated) high-throughput applications.

Currently, there is a need for robust procedures for differential labeling of peptides that can support both large-scale analyses in proteome research as well as routine (diagnostic) testing. It is therefore desirable that such labeling procedures offer high specific labeling of amino acids target residues, high coverage of the proteome, and robust labeling conditions. Also, labeling should not lead to complex mass spectra, i.e. not too many amino acid residues should be labeled. Labeling of the selected amino acids can preferably be performed in a saturated fashion, the heavy isotope labeled molecule should preferably have identical chromatographic characteristics as light labeled molecule, e.g. same retention time, heavy isotope labeled molecule should preferably have identical ionization characteristics as the light labeled molecule, and labeling should ideally not interfere with enzymatic digestion of proteins.

It is further desirable that upon differential labeling, the products can be separated by alternative means than by affinity chromatography before being subjected to mass spectrometry. A further desired improvement over the current technology is the omission of the purification step prior to MS. Instead, it would be advantageous if differentiation between labeled and non labeled molecules can be made during MS-MS.

Surprisingly, it has been found that a labeling method wherein use is made of a labeled transition metal complex in accordance with the present invention fulfils one or more of these needs. Said method results advantageously in a bond between entity and label that survives the ionisation process of mass spectrometry.

Accordingly, the novel category of labeled transition metal complexes in accordance with the present invention can advantageously be used as tags in methods for differential labeling of bio-organic molecules. They constitute improvements over existing reagents for differential expression labeling and circumvent the various problems of the prior art reagents.

The present invention also relates a method for rendering a chemical or biological entity distinguishable by mass spectrometry, said method comprising the step of differentially labeling said entity with at least one labeled transition metal complex in accordance with the present invention.

The present invention further relates to the use of a labeled transition metal complex in accordance with the invention for creating a defined shift in the molecular weight of the chemical or biological entity in order to facilitate mass spectrometric analysis of said entity or a sample comprising said entity.

The creation of a defined shift in the molecular mass of a chemical or biological entity upon binding of a labeled transition metal complex will ultimately result from the attachment of the labeled transition metal complex thereto. Therefore, said shift will essentially coincide with an change in the mass of the entity that is proportional to the mass of the labeled transition metal complex minus the mass of the leaving portion of a leaving group. Said mass change can be determined by mass spectrometric analysis.

The present invention also relates to a method for rendering chemical or biological entities distinguishable by mass spectrometry according to the invention comprises the differential labeling of said entities with at least one labeled transition metal complex, wherein suitable labeled transition metal complexes are those as described hereinbefore. The use herein of two different labeled transition metal complexes, each having its own labeling specificity, allows for the possibility of differentially labeling different entities within one sample.

Another aspect, the present invention relates to a method for mass spectrometric analysis of a chemical or biological entity, said method comprising the steps of differentially labeling said entity with at least one labeled transition metal complex in accordance with the invention and analyzing said entity by mass spectrometry.

In preferred embodiments of methods of the present invention said chemical or biological entities originate from different samples.

In yet other preferred embodiments of methods of the present invention said step of differentially labeling said entities is performed with at least two labeled transition metal complexes in accordance with the present invention, wherein said labeled transition metal complexes are of different molecular mass, said difference in molecular mass being ≥1 Da.

In preferred embodiments of methods of the present invention said labeled transition metal complexes display the same labeling characteristics, the same properties in liquid chromatography (LC), e.g. same hydrophobicity or hydrophilicity, and the same metal oxidation state.

In yet other preferred embodiments of methods of the present invention labeled transition metal complexes containing a spacer are suitable in parent ion scanning or neutral loss scanning in mass spectrometry.

In yet other preferred embodiments of methods of the present invention the transition metal isotope fingerprint may be used as an identification tool of labeled entities.

The molecular mass difference between said labeled transition metal complexes may be due to the presence or absence of specific isotopes, atoms, groups of atoms, molecules, or groups of molecules in any part of the transition metal complexes, or ligands, spacers, reactive moieties and/or markers attached thereto.

In preferred embodiments of the invention said molecular mass difference between said labeled transition metal complexes is due to the presence of different stable isotopes in said complexes, e.g. wherein a first labeled transition metal complex comprises a light isotope and at least a second labeled transition metal complex comprises a heavy isotope.

The stable isotopes that cause the difference in molecular mass may be comprised in any part of the labeled transition metal complexes. They are suitably contained in the inert tridentate moiety or attached to the tridentate moiety by means of a spacer.

In another aspect, the present invention provides a set of said at least two labeled transition metal complexes of different molecular mass.

A further aspect of the present invention relates to a kit of parts comprising a set of at least two labeled transition metal complexes of different molecular mass. Preferably, the difference in molecular mass results from the presence of at least one different stable isotope between said transition metal complexes.

A "chemical or biological entity" as used herein is to be interpreted as something that comprises one or more sulphur, oxygen, phosphorus, and/or nitrogen containing reactive sites, including entities which have been modified to contain such reactive sites (e.g. by incorporation of serine, threonine, or tyrosine residues).

"Entity" further relates to a micro-organism, a virus or a prion, or to a material comprising one or more of said sulphur reactive, phosphor reactive, oxygen reactive or nitrogen reactive types of reactive sites, or a product made thereof, such as a micro-array, a microtitre plate, a test strip or a test tube. In particular an entity relates to an inorganic or organic compound, including a bio-organic compound.

A "bio-organic molecule" as used herein refers to a biological carbon containing molecule. Also, a bio-organic molecule refers to a compound capable of inducing or affecting an action in a biological system, e.g. by inducing or affecting a therapeutic or prophylactic effect, an immune response, a metabolic process etc.

The term "labeling" is used herein to refer to the process of coupling/attaching the labeled transition metal complex to an entity.

The term "differential labeling" is used herein to refer to the labeling reaction resulting in an unequal distribution of the marker between reactive sites, between entities or between samples. Differential labeling may result in one entity having different markers at distinct reactive sites, e.g. an entity having its P-, O-, S- and N-reactive sites differentially labeled. Differential labeling may also result in identical entities from one sample having different markers or having different marker densities, e.g. one sample may have identical proteins that are differentially labeled. Also, differential labeling may result in identical entities from two samples having different markers or having different marker densities. Such a type of differential labeling is very suitable for comparative analysis of proteomes, genomes, or metabolites between cells.

A "marker", "tag", or "label" as used synonymously herein may be any moiety that can be attached to the entity via the transition metal complex, and that can be used to detect, monitor or visualize the entity.

A "residue" of a compound as used herein should be interpreted as the compound itself or as part of a larger entity, e.g. an amino acid residue in a protein.

A "different stable isotope" is herein defined as an alternative isotope of an atom that is stable and is not the isotope of said atom which is most abundant in nature. In the case of C (carbon) $^{13}C$ (1.07%) would be a different stable isotope, as opposed to the normally occurring $^{12}C$ (98.93%). In case the transition metal is, for instance, Pt (platinum), $^{192}Pt$ (0.79%), $^{194}Pt$ (32.9%), $^{196}Pt$ (25.3%), and $^{198}Pt$ (7.2%) are different stable isotopes as opposed to the normally occurring and $^{195}Pt$ (33.8%).

An entity linked to the labeled transition metal complex may be referred to as a Me-S adduct (when attached to a sulphur containing reactive site), to a Me-N adduct (when attached to a nitrogen containing reactive site), or in general to a Me-adduct.

A sulphur containing reactive site may hereafter be referred to as a S-reactive site, and a nitrogen containing reactive site may hereafter be referred to as N-reactive site. Likewise, an oxygen containing reactive site may be referred to as an O-reactive site, and a phosphorus containing reactive site may be referred to as P-reactive site.

It is well known in the art that a chemical or biological entity may be labeled with a detectable marker to identify, detect, visualize, separate, purify, isolate, quantify or monitor the entity e.g. in chemical, biological or medical research or diagnosis. A wide variety of labeling methods are known from the art (for a review see Hermanson, 1996, Bioconjugate techniques, Academic Press, ISBN 0-12-342335-X). Many factors may play a role in choosing a particular detectable marker and a particular method of labeling. Such factors include the nature of the entity, the conditions of the labeling reaction, the sensitivity during the labeling reaction, the specificity towards the entity and the detection limits of the labeled entity.

The reactivity of labeled transition metal complexes towards a variety of reactive sites is a benefit in many applications, since it may allow fast labeling reactions and an excellent sensitivity towards a wide variety of entities.

The present inventors have found that a particular advantage of the use of labeled transition metal complexes as linkers in labeling reactions over such linkers as N-hydroxysuccinimide (NHS) and maleimide is that the labeled transition metal complexes in accordance with the present invention are routinely applicable in mass spectrometry applications. Furthermore, the specific composition and ratio between the most abundant transition metal atom and its different stable isotopes can provide for a defined tool in identifying labeled entities in mass spectrometry. A further advantage of the use of the present labeled transition metal complexes in labeling reactions is that, depending on the reactive moieties used, such complexes may support the labeling of a wide variety of chemical entities.

Another advantage is that proteins may be labeled by a suitable labeled transition metal complex at histidine (His), methionine (Met) and/or cysteine (Cys) residues. This provides for the possibility to label more side groups in a peptide chain and thus to achieve higher labeling densities. This may also allow for the labeling of additional amino acid residues in a peptide chain.

Not all biological proteins and/or peptides comprise cysteine, and cysteine labeling will allow for the detection of only 85% of the proteins in the proteome. The possibility to label methionine residues will allow for the detection of 97% of the proteins in the proteome. In combination, the use of the labeling complexes of the present invention now provides for a proteome coverage of 98.35%. Thus, the possibility of choosing new target amino acids represents an important advancement in proteome research.

Moreover, the specificity of the labeling reaction with the labeled transition metal complexes according to the invention may be controlled such as to discriminate between labeling of sulphur containing reactive sites and nitrogen containing reactive sites in a chemical or biological entity. Therefore, by using the labeled transition metal complexes according to the present invention one can direct the labeling of an entity towards a specified reactive site within an entity or a group of entities that together comprise a variety of reactive sites.

In one embodiment of a use of a labeled transition metal complex according to the invention, the chemical or biological entities in a sample may be differentially labeled according to a method described in European patent application 1 262 778.

In a preferred embodiment the use of a labeled transition metal complex according to the invention comprises the differential labeling of chemical or biological entities present in two different samples of which the composition is to be compared. A preferred use includes the measurement of the protein expression profile, or proteome in a test sample, in order to compare the results thereof with corresponding results from a reference sample.

Yet another advantage of the use of labeled transition metal complexes in differential labeling procedures of proteins is that there is no interference with the subsequent trypsin digestion. This is especially advantageous in labeling procedures of cellular proteomes that are subjected to trypsin digestion for the provision of peptides of suitable length for MS analysis.

Apart from the possibility to label entities originating from one sample, i.e. said entities occurring as a mixture, the chemical or biological entities may also originate from different samples. The differential labeling may for instance comprise the labeling of entities in a test sample, without labeling the entities in the reference sample or vice versa. Identical entities present in both samples then become distinguishable by mass spectrometry as a result of the defined shift in the molecular mass of the entities in the test sample. Alternatively, the differential labeling may also comprise the labeling of entities in both samples. In such instances, rendering said entities distinguishable by mass spectrometry will involve the differentially labeling of said entities with at least two labeled transition metal complexes of different molecular mass.

A method for differential labeling may be performed in a wide variety of buffered solution and over a wide pH range. Suitable buffered solutions include all commonly used buffers such as TRIS/Glycine and phosphate buffers. Detergents such as Tween-20, Triton X-100 or SDS may be present in the labeling mixture. The presence of salts, such as sodium, potassium or ammonium salts of chloride, nitrate, sulphate or phosphate, at concentrations at which they are commonly used, hardly affects the labeling reaction. Preferred buffers for labeling in MS are those that do not leave residual traces after evaporation, e.g. buffers containing ammonium acetate and the like.

The reaction parameters for the differential labeling reaction may also be chosen such that an entity is differentially labeled and include the choice for a specific pH value. The pH as used herein should be interpreted as the pH value of a solution in water at 20° C. In general, the formation of Me-S adducts is pH independent whereas formation of Me-N adducts is pH dependent. In a preferred embodiment one or more S-reactive sites are selectively labeled over one or more nitrogen containing sites by making use of the pH.

As a guideline, one may choose the pH of the labeling reaction at a pH below the lowest pKa of any of an entity's N-reactive sites that should not be labeled, allowing differential labeling of one or more S-reactive sites. As the skilled professional will understand other factors, besides pKa, may play a role, including the influence of the micro-environment in the vicinity of an entity that is to be labeled. In general, S-reactive sites are differentially labeled over N-reactive sites at acidic pH.

In theory, the formation of a Me-S adducts is a one step process. A reactive group leaves the platinum complex upon S donating an electron pair to platinum. This process, the direct conversion Me-X into Me-S, is believed to be pH independent. On the other hand, N donors require replacement of a reactive group of the platinum complex by oxygen prior to N substitution. First, Me-X becomes Me-O and eventual Me-N. This is a two step scheme in which the first step can be controlled by changing pH. Factors influencing pH of a solution may therefore interfere with Me-N adduct formation.

The presence of ions may also be used to control the selectivity of the transition metal complex for N-reactive sites. In an embodiment one or more leaving ligands, preferably anionic moieties, are used in the inhibition of labeling a labeled transition metal complex to a N-reactive site, in order to enhance differentiated labeling of a S-reactive site. Preferred examples of such leaving ligands include $Cl^-$, $NO_3^-$, $HCO_3^-$, $CO_3^{2-}$, $SO_3^{2-}$, $ZSO_3^-$, $I^-$, $Br^-$, $F^-$, acetate, carboxylate, phosphate, ethyl nitrate, oxalate, citrate, a phosphonate, $ZO^-$, and water. Z is defined herein as a hydrogen moiety or an alkyl or aryl group having from 1 to 10 carbon atoms. Particularly good results have been achieved by using salts comprising an anionic moiety, of which chloride is particularly preferred. The counter ions are preferably alkali cations, alkali earth cations or cations also used to direct the labeling. In a preferred embodiment the total ionic strength of said anionic moieties used in the inhibition of labeling to a N-reactive site is at least 0.1 mol/l. More preferably the total ionic strength is in the range of 0.1 to 0.5 mol/l.

The presence of transition metal ions, may also be used for selection of the reactive site to be labeled. In particular such ions have been found suitable to prevent or slow down labeling of an S-reactive site or to make a labeled Me-S adduct labile, so that effectively one or more N-reactive sites are differentially labeled over said S-reactive site. This form of differential labeling of entities or samples may hold specific advantages when only a subset of entities is to be analyzed.

In addition to the parameters as mentioned above a method according to the invention may further be fine tuned by parameters such as temperature, preferably varied in the range between 0° C. and 120° C., more preferably in the range between 20° C. and 70° C.; reaction time, commonly in the range between 1 min and 48 hours, preferably in the range between 10 rain and 24 hours, more preferably in the range between 25 min and 15 hours; concentration of the reagents, molar ratio of the reagents, overall net charge of the labeled transition metal complex, and the like. These parameters may be adjusted depending upon the particular application in any way known in the art. The overall net charge of the labeled transition metal complex, for example, affects the specificity of Me-N adduct formation in histidine at neutral pH. Neutral Me-complexes, such as fluorescein- and cyanine transition metal complexes, form Me-N adducts whereas positively charged transition metal labeling complexes, e.g. rhodamine- and dinitrophenol Me complexes, do not or less efficient. Positively charged labeled transition metal complexes display differential labeling towards N adducts above the isoelectric point of the peptide, protein, and the like. Apart from allowing the selective labeling of N-reactive sites over S-reactive sites or vice versa, a method according to the present invention also makes it possible to differentiate between distinct N-reactive sites or distinct S-reactive sites, by choosing the correct conditions, such as described in European Patent Application 1 262 778.

The above instructions for differential labeling of a single entity may also be employed to obtain the required or optimal labeling for differential labeling of different compounds, and from compounds of different origin.

A method for mass spectrometric analysis of the chemical or biological entities according to the invention must first render such entities distinguishable by MS and thus involves a first step of differentially labeling the entities with at least one labeled transition metal complex as described above. Further, such a method involves the step of analyzing the molecular mass of said entities by mass spectrometry. The skilled person is knowledgeable about the various possibilities of MS detection.

Prior to MS detection, entities from different samples may optionally be mixed and the mixture be subjected to MS analysis. The advantage of mixing differentially labeled entities or samples prior to MS analysis is that the MS conditions are equal for all entities tested and the shift in the molecular mass can be easily discerned.

Also, prior to MS detection, labeled entities may be purified from unlabeled entities by e.g. affinity isolation of the affinity tagged materials, or particularly in methods of the present invention by ion exchange chromatography, or by using fluorescent markers in combination with fluorescence-activated cell sorting (FACS). Furthermore, the labeled transition metal complexes of the present invention offer the opportunity to separate (differential) labeled entities during MS-MS without prior purification.

In methods involving sample comparison, it is therefore preferred that both samples are labeled with labeled transition metal complexes of different molecular mass in order to allow a purification step to be performed on both said samples. In this way, purification bias is equal for both samples. As an affinity label any label capable of binding to a capture reagent may be used. In preferred embodiments of the present invention the affinity label is a biotin, or initrophenol (DNP), fluorescein or Dyomics 647 dye and the preferred capture reagent is a strepavidin or avidin, anti-DNP, anti-fluorescein, and anti-Dyomics 647, respectively. After affinity isolation of affinity tagged materials, some of which may be isotopically labeled, the interaction between the affinity label and the capture reagent is disrupted or broken to allow MS analysis of the isolated materials. The affinity label may be displaced from the capture reagent by addition of displacing ligand, which may be free affinity label or a derivative of said affinity label, or by changing solvent (e.g., solvent type or pH) or temperature conditions or the linking complex may be cleaved chemically, enzymatically, thermally or photochemically to release the isolated materials for MS analysis.

Prior to MS detection, the labeled entities are separated to allow the detection of preselected species of molecules. Prior separation, for instance by liquid chromatography (LC) or gas chromatography (GC), will enable the analysis by MS of a complex mixture of proteins. The skilled person will be able to determine required or optimal separation procedures for the specific application.

A method for mass spectrometric analysis of the chemical or biological entities may comprise the comparative analysis of a test sample and a reference sample. When after differential labeling, the two samples are admixed and the mixture subjected to chromatographic separation followed by mass spectrometric analysis, the entities labeled with the labeled transition metal complex will exhibit a predictable molecular mass shift compared to the non-labeled entities. As such, the said method of the invention allows comparative mass spectrometric analysis of the chemical or biological entities between samples.

In order to distinguish entities of a test sample from entities of a reference sample on the basis of their molecular mass, such a method may also comprise the provision of at least two labeled transition metal complexes of different molecular mass and the differential labeling of said entities between said samples. In other words, the test sample entities are labeled with a labeled transition metal complex of a first molecular mass, and the reference sample entities are labeled with a labeled transition metal complex of a second molecular weight. Depending on the resolution required, a difference in molecular mass between the labeled transition metal complexes of 1 Da may suffice. Advantageously, the difference in molecular weight between the labeled transition metal complexes in said set is more than 2, more advantageously more than 4, preferably more than 6, more preferably more than 8, and even more preferable more than 10 Da.

The purpose of the two labeled transition metal complexes with different molecular mass is to generate pairs or sets of reagents that are substantially chemically identical, but which are distinguishable by mass.

The difference in molecular mass may be brought about by substituting atoms or ligands of the transition metal complexes with atoms or ligands of higher or lower molecular mass. Suitable mass-altering ligands include aliphatic groups, carbohydrates, alcohol functionalities, and halogens such as for example F, Cl and Br.

The difference in molecular mass may also be brought about by substituting atoms of the transition metal complexes with alternative stable isotopes. Thereto, the transition metal complexes may be differentially isotopically labeled, e.g., by substitution of one or more atoms in the complexes with a stable isotope thereof. For example, hydrogens can be substituted with deuteriums, $^{12}C$ with $^{13}C$, $^{14}N$ with $^{15}N$, $^{195}Pt$ with $^{192}Pt$, $^{194}Pt$, $^{196}Pt$ or $^{198}Pt$, $^{16}O$ with $^{18}O$, etcetera. Also P or S atoms present in the complex may be substituted. In preferred embodiments use is made of $^{1}H$ and $^{2}H$, or $^{12}C$ and $^{13}C$, or $^{14}N$ and $^{15}N$, or $^{16}O$ and $^{18}O$, or combinations thereof. Furthermore, using the mixture of transition metal isotopes, e.g. Pt isotopes, will give a unique pattern of mass distribution making the discerning of labeled entities easier.

In yet another alternative embodiment, the marker attached to the transition metal complex may provide that complex with a difference in molecular mass by ways as described above. As such, the molecular mass difference may be attributed to (the presence of) the marker. In a preferred embodiment complexity is reduced by making use of monoisotopic platinum and $^{15}N$, $^{13}C$ and/or D labeled ligand(s).

The present invention relates to a set of at least two transition metal complexes of different molecular mass as described above. Such a set can be used for qualitative and particularly for quantitative analysis of global protein expression profiles in cells and tissues.

In yet another aspect, the present invention relates to a transition metal complex comprising at least one different stable isotope as described above.

The invention further relates to a chemical or biological entity labeled with the labeled transition metal complex comprising at least one different stable isotope. Preferably, said entity is an amino acid, peptide or protein.

The transition complexes according to this invention are highly suitable for (absolute) quantification. This is a method to determine the absolute amounts of entities in a single sample using internal entity standards. The focus in such method is on a specific entity of interest, or its modification state. The method does not require the entity to be labeled, however it does require specific internal standards to be prepared prior to mass spectrometry analysis. Suitable internal standards are entities with similar is not identical features as the entity under investigation.

A further aspect of the present invention relates to a kit of parts comprising a set of said at least two transition metal complexes of different molecular mass. Preferably, the difference in molecular mass results from the presence of different stable isotopes in said transition metal complexes. The kit of parts may further comprise reaction instructions, one or more test samples, one or more other reagents, one or more test tubes or strips and the like, and one or more preparations selected from the group formed, buffers, marker preparations and preparations for adjusting the ionic strength. Such a kit is very suitable for employing a method according to the invention.

The present invention provides analytical reagents and mass spectrometry-based methods using these reagents for the rapid, and quantitative analysis of proteins or protein function in mixtures of proteins. The analytical method can be used for qualitative and particularly for quantitative analysis of global protein expression profiles in cells and tissues, i.e. the quantitative analysis of proteomes. The method can also be employed to screen for and identify proteins whose expression level in cells, tissue or biological fluids is affected by a stimulus (e.g., administration of a drug or contact with a potentially toxic material), by a change in environment (e.g., nutrient level, temperature, passage of time) or by a change in condition or cell state (e.g., disease state, malignancy, site-directed mutation, gene knockouts) of the cell, tissue or organism from which the sample originated. The proteins identified in such a screen can function as markers for the changed state. For example, comparisons of protein expression profiles of normal and malignant cells can result in the identification of proteins whose presence or absence is characteristic and diagnostic of the malignancy.

The invention will now further be illustrated by the following non-limiting examples.

EXAMPLES

I. Preparation of Tridentate Ligands and Transition Metal Complexation

Ligands of the following type, their complexation with $K_2PtCl_4$, and the subsequent BOC-deprotection of the resulting complex for reaction with NHS esters and incorporation of a marker is described.

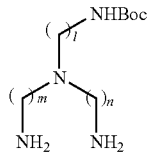

where l≥6, m=2 or 3, and n=3 or 2 if m≠2

Figure 5:
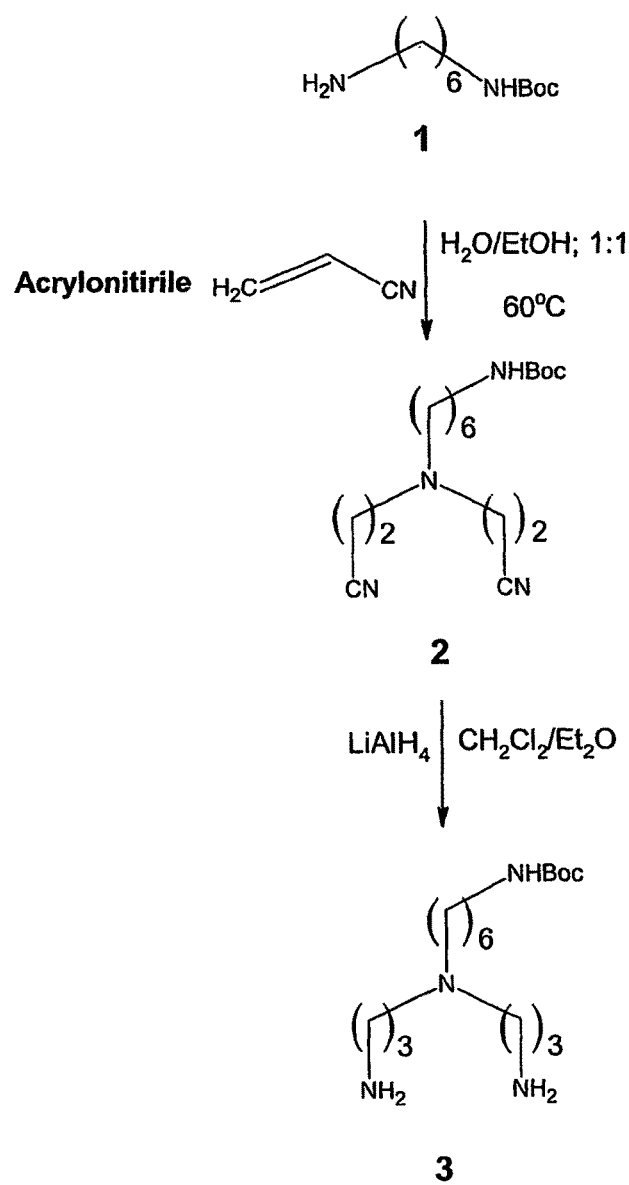
FIG. 5 depicts synthesis of compound 3.

Synthesis of 2 (FIG. 5: Scheme 1) (the Bold Face Type Numbers Indicate the Compounds as Shown in the Figures and Schemes Referred to, E.G. in the Present Example to Those of FIG. 5: Scheme 1)

1, N-Boc-hexane-1,6-diamine, (140.5 mg, 649.5 µmol) was dissolved in a mixture $H_2O$/EtOH 1/1 (20 ml). Acrylonitrile (425.5 µl, 6.495 mmol) was added to the resulting solution. The mixture was refluxed overnight at 60° C. and taken to dryness to afford pure an oily pale brown material. The residues were dissolved in $CH_2Cl_2$ and dried over $MgSO_4$. 2 was obtained following filtration and removal of the solvents under reduced pressure. (Yield: 166.8 mg, 95%). $^1H$ NMR ($CDCl_3$): δ 1.35 (4H, m, $NH(CH_2)_2(CH_2)_2$); 1.43 (13H, m, $NH(CH_2)(CH_2)CH_2)_2(CH_2)$+tBu); 2.60 (6H, m, $NH(CH_2)(CH_2)_5$+$(CH_2)(CH_2)CN$); 2.94 (4H, m, $CH_2CN$); 3.1 (2H, m, $(CH_2)NHBoc$); 4.55 (1H, broad peak, NHBoc).

Synthesis of 3 (FIG. 5: Scheme 1)

2 (153.0 mg, 474.5 µmol) was dissolved into $CH_2Cl_2$ (20 ml). After stirring the solution at 0° C. for 30 minutes, a solution of $LiAlH_4$ in $Et_2O$ (1M, 2.9 ml, 2900 µmol) was added drop wise. The mixture was stirred at 0° C. for 90 minutes and allowed to reach ambient temperature. The excess of $LiAlH_4$ was carefully destroyed by the addition of 4 ml of water in a drop wise manner. The Li salts were removed by filtration, and washed with water (10 ml) and $CH_2Cl_2$ (10 ml). The aqueous layer was separated and extracted with $CH_2Cl_2$ (3*10 ml). The organic extracts were combined, dried over $MgSO_4$ and taken to dryness under reduced pressure to yield 3 as a colourless oil (yield: 99.3 mg, 63%). $^1H$ NMR ($CDCl_3$): δ 1.23 (4H, m, $NH(CH_2)_2(CH_2)_2$); 1.38 (13H, m, $NH(CH_2)(CH_2)CH_2)_2(CH_2)$+tBu); 1.52 (4H, m, $(CH_2)(CH_2)NH_2$); 2.32 (2H, m, $N(CH_2)(CH_2)_5$); 2.44 (4H, m, $N(CH_2)(CH_2)_2NH_2$); 2.74 (4H, m, $CH_2NH_2$); 3.02 (2H, m, $(CH_2)NHBoc$); 3.30 (4H, broad peak, $NH_2$); 4.72 (1H, broad peak, NHBoc).

Figure 7:
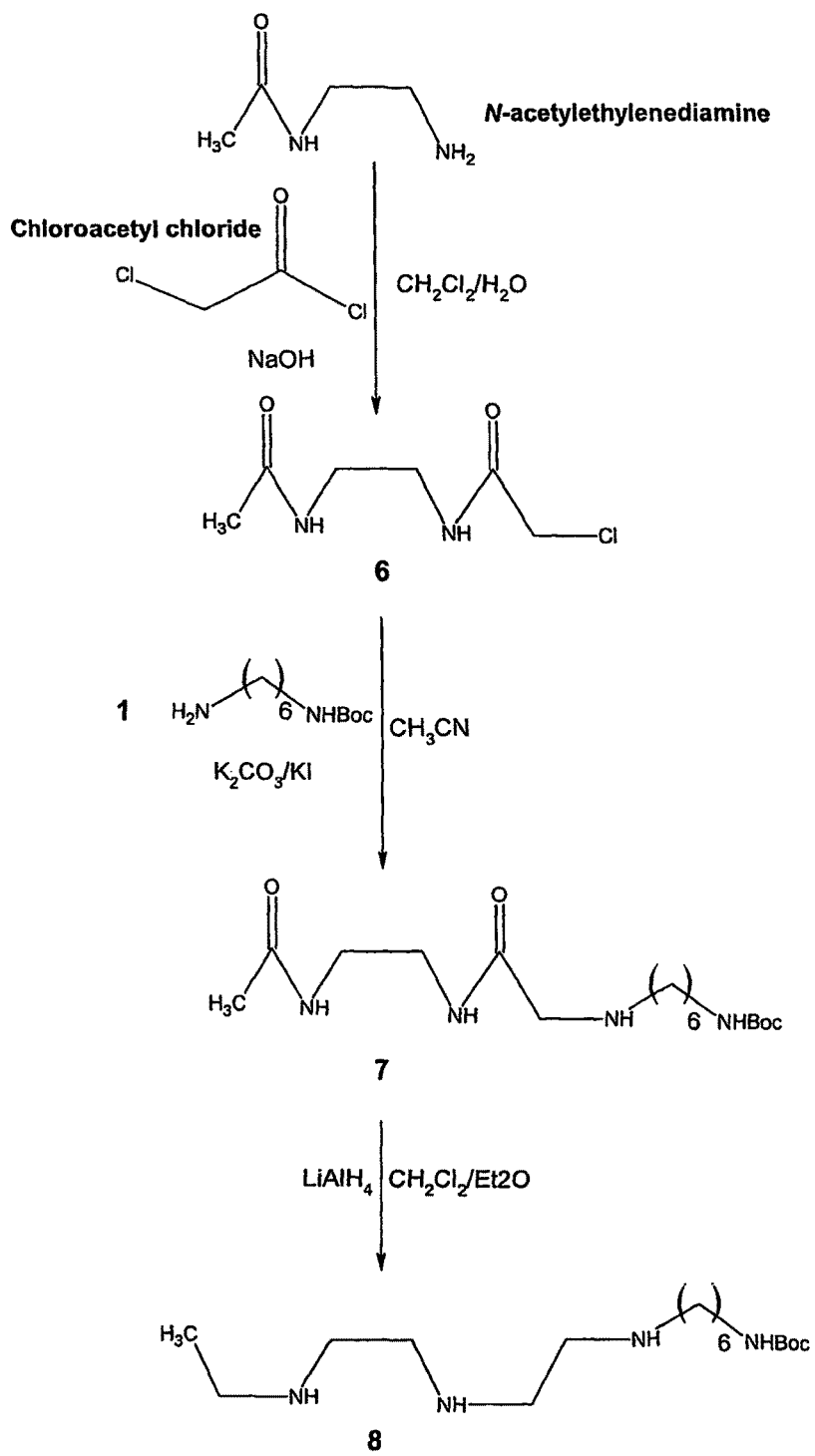
FIG. 7 depicts synthesis of compound 8.

Synthesis of 6 (FIG. 7: Scheme 3)

A solution of 165 µl (233.97 mg, 2.072 mmols) of chloracetyl chloride in 70 ml of $CH_2Cl_2$ was added at a rate of 5 drops per second and at ambient temperature to a mixture of 198.50 µl (211.60 mg, 2.071 mmols) of N-acetylethylenediamine, 140 ml of $CH_2Cl_2$ and 2071.6 µl (80.77 mg, 2.072 mmols) of a 1 M solution of NaOH in water. After the addition was complete, the resulting mixture was stirred overnight at room temperature. The solvents were removed under reduced pressure. The solids were washed with MeOH and the NaCl salts were separated via centrifugation. The clear MeOH extracts were then taken to dryness under reduced pressure and the washings with MeOH and centrifugation steps were repeated until no NaCl could be separated. The MeOH extracts were taken to dryness under reduced pressure which afforded 6.

Synthesis of 7 (FIG. 7: Scheme 3)

A solution of 6 (1 mmol per 17 ml) in MeCN was added at a rate of 5 drops per second and at 75° C. (reflux condenser introduced on top of the flask into which the solution of 6 is added) to a mixture containing 3 (relative to the number of moles of 6) equivalents of $K_2CO_3$, 1 molar equivalent (relative to the number of moles of 6) of KI and 1 molar equivalent (relative to the number of moles of 6) of 1, N-Boc-hexane-1,6-diamine in MeCN (1 mmol of 1 per 34 ml). After addition was complete, the mixture was allowed to reflux overnight. The solvents were then removed under reduced pressure. The solids were washed with $CH_2Cl_2$ and the $K^+$ salts were filtered. The $CH_2Cl_2$ extracts were taken to dryness under reduced pressure which afforded 7.

Synthesis of 8 (FIG. 7: Scheme 3)

The procedure described for the preparation of 3 was repeated using 7 instead of 3 which afforded 7.

General Protocol for the Complexation of Boc Tridentate Ligands (3 in Scheme 2 (FIG. 6) and 8 in Scheme 4 (FIG. 8)) with $K_2PtCl_4$ $K_2PtCl_4$ and 1 molar equivalent of L, where L is the tridentate ligand used, were added to DMF (4.69*10$^{-6}$ mol of $K_2PtCl_4$ per ml). The mixture was then heated at 40° C. overnight during which the red $K_2PtCl_4$ salts dissolved. The solution was taken to dryness and the $K^+$ salts were washed with water. The insoluble solids were filtered and washed with $Et_2O$ before being dried under reduced pressure.

4: $^{195}Pt$ NMR (MeOD): $δ_{Pt}$ −2520 ppm. MS (EI$^+$): m/z 561 [M−Cl]$^+$

General Protocol for the Boc-Deprotection and the Subsequent Incorporation Incorporation of a Marker on Pt Complexes 126 µmol of [Pt(L)Cl]Cl were dissolved in 200 mM HCl (3 ml). The resulting solution was then stirred at 50° C. overnight. The pH was brought to 8 by the addition of 1 M NaOH. 5*succinimide coupling buffer (2 ml) was then added to the solution. The NHS-succinimide ester (63 µmol) in DMF (5 mL) was subsequently added drop wise. The resulting solution is stirred overnight at ambient temperature under protection from light. The species dissolved at a concentration of 1 mg/ml is then purified through a Sephadex column (G15) and obtained on removal of the solvents under reduced pressure. 4 after Boc deprotection: $^{195}$Pt NMR (MeOD): $\delta_{Pt}$ −2512 ppm. MS (EI$^+$): m/z 461 [M−Cl]$^+$ II. Complexation of K$_2$PtCl$_4$ with Diethylenetriamine Diethylenetriamine is commercially available (Aldrich, cat #D9, 385-6). K$_2$PtCl$_4$ (1 g) was dissolved in milli-Q (25 ml). The small yellow crystals and the grey material that did not dissolve were filtered. Diethylenetriamine (0.5 ml) was added to the resulting clear red solution. The pH was adjusted to 3 using a solution of HCl in water (6 M). The solution was refluxed for 6.5 hours. After 2 hours of reaction, the pH was adjusted to 4 using solutions of NaOH in water (1 and 5 M). The reaction mixture was allowed to cool at room temperature overnight. The pH then was acidified to 1 using a solution of HCl in water (6 M). The reaction mixture then was put in the freezer (−20° C.) for 72 hours. White crystals formed and were filtered. The pH of the filtrate was brought to 6, some solvent was evaporated and the resulting solution was cooled in an ice bath. This gave a second set of crystals that were filtered. $^{195}$Pt NMR (D$_2$O): $\delta_{Pt}$ −2722 ppm.

III. Preparation of APET Complexes

Preparation of the 4'-aminopentyl ether-2,2':6',2"-terpyridine (2)

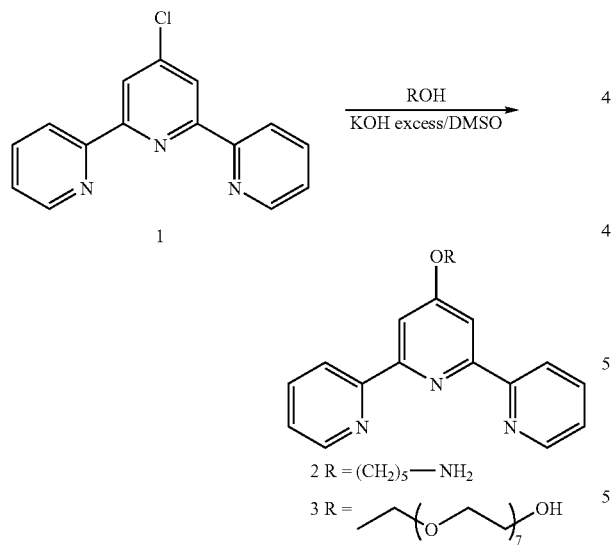

To a stirred suspension of 986 mg (17.6 mmol, 4.7 eq) of powdered KOH in dry DMSO (20 ml) at 80° C., 385.8 mg of 5-amino pentanol (3.74 mmol, 1 eq) was added. After the alcohol addition, the solution changed from orange to brown. After 30 min, 1 g of 4'-chloro-2,2':6',2" terpyridine (3.74 mmol, 1 eq) was added. After 4 h for 2 and 18 h 30 for 3 of stirring at 80° C. the solution was poured in 200 ml of cold Milli Q. The aqueous layer was extracted with CH$_2$Cl$_2$ (3*20 ml). The combined organic phases were dried over Na$_2$SO$_4$ and evaporated by rotary evaporator. The yield of the product was 908.4 mg yellow particles (73%).

$^1$H NMR (CDCl$_3$)

δ 1.3 [broad peak, 2H, CH$_2$], 1.9 [broad peak, 2H, CH$_2$], 2.2 [broad peak, 2H, CH$_2$], 2.5[broad peak, 2H, CH$_2$], 2.6 [broad peak, 2H, NH$_2$], 3.6 [t, 2H, CH$_2$], 6.8 [dd, 2H, H$_{4,4"}$], 7.3 [t, 2H, H$_{5,5"}$], 7.42 [s, 2H, H$_{3',5'}$], 7.9 [dd, 2H, H$_{3,3"}$], 8.1 [d, 2H, H$_{6,6"}$].

$^{13}$C NMR (CDCl$_3$)

δ 23.5 [CH$_2$], 29.09 [CH$_2$], 33.4 [CH$_2$], 42 [CH$_2$—NH$_2$], 68.4 [CH$_2$—O], 107.5 [CH, C$_{3',5'}$], 121.5 [CH, C$_{5,5"}$], 124.3 [CH, C$_{3,3"}$], 137.2 [CH, C$_{4,4"}$], 149.3 [CH, C$_{6,6"}$], 156.03 [C, C$_{2,2"}$], 157.1 [C, C$_{2',6'}$], 167.3 [C, C$_{4'}$].

UV/Visible Absorption (CHCl$_3$)

$\lambda_{max}$ 245 nm ($\epsilon$ 16 500 M$^{-1}$·cm$^{-1}$)

279 nm ($\epsilon$ 16 500 M$^{-1}$·cm$^{-1}$)

Preparation of the 4'-polyethylene glycol ether-2,2':6',2" terpyridine (3)

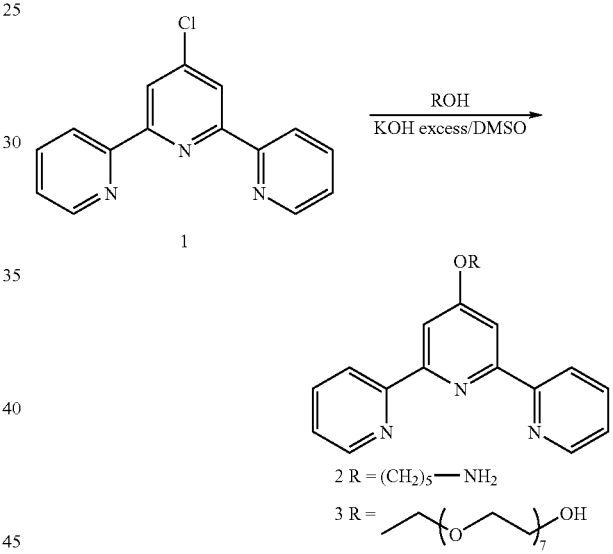

To a stirred suspension 98.6 mg of powdered KOH (1.76 mmol, 4.7 eq) in dry DMSO (20 ml) at 80° C., 112.2 mg of PEG 300 (0.374 mmol, 1 eq) was added. After 30 min, 100 mg of 4'-chloro-2,2':6',2" terpyridine was added (0.374 mmol, 1 eq). After 20 h of stirring at 80° C. the solution was poured in 200 ml of cold Milli Q. The aqueous layer was extracted with CH$_2$Cl$_2$ (3*20 ml). The combined organic phases were dried over Na$_2$SO$_4$ and evaporated by rotary evaporator. The yellow oil was obtained with yield of 35% (68.3 mg).

$^1$H NMR (CDCl$_3$)

δ 3 [broad peak, 1H, OH], 3.67 [2H, CH$_2$], 3.60 [m, 6H, CH$_2$], 3.86 [t, 2H, CH$_2$], 4.33 [t, 2H, CH$_2$], 7.24 [t, 2H, H$_{5,5"}$], 7.74 [dd, 2H, H$_{4,4"}$], 7.95 [s, 2H, H$_{3',5'}$], 8.5 [dd, 2H, H$_{3,3"}$], 8.6 [d, 2H, H$_{6,6"}$].

$^{13}$C NMR (CDCl$_3$)

δ 62.2 [CH$_2$—O], 68.5 [CH$_2$—O], 71.3 [CH$_2$—O], 71.6 [CH$_2$—O], 73.5 [CH$_2$O], 108.2 [CH, C$_{3',5'}$], 122.06 [CH, C$_{5,5"}$], 124.60 [CH, C$_{3,3"}$], 137.54 [CH, C$_{4,4"}$], 149.73 [CH, C$_{6,6"}$], 156.7 [C, C$_{2,2"}$], 157.7 [C, C$_{2',6'}$], 167.7 [C, C$_{4'}$].

Coupling Between Fluorochrome (or Hapten) with APET (6a-d)

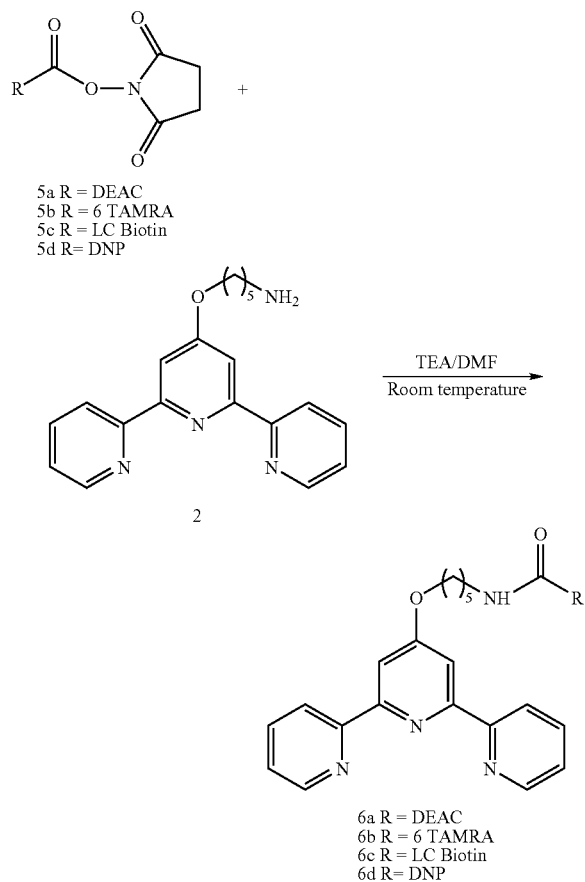

5a R = DEAC
5b R = 6 TAMRA
5c R = LC Biotin
5d R = DNP

6a R = DEAC
6b R = 6 TAMRA
6c R = LC Biotin
6d R = DNP

In a micro reactor equipped with a magnetic stirring device the APET was dissolved in 300 μl of DMF. 1 eq of the dye and 3 eq of TEA were added and the solution was stirred at room temperature for 20 h in the dark. The solvent was removed. The purity of the products was checked by RP HPLC and the products were purified by preparative RP HPLC with the acetonitrile/TEAA buffer on Luna 10 C18 (2).

Yield:

TABLE 1

Yield obtained for the ligand 6a-d

| | Fluorochrome (or Hapten) | m (mg) | Yield |
|---|---|---|---|
| 6a | DEAC | 7.2 | 97% |
| 6b | 6 TAMRA | 3.1 | 55% |
| 6c | LC Biotin | 5.8 | 78% |
| 6d | DNP | 3.5 | 51% |

$^1$H NMR (CDCl$_3$)

DEAC (6a):

δ 1.24 [t, 6H, CH$_3$], 1.66 [Quintuplet, 2H, CH$_2$], 1.73 [Quintuplet, 2H, CH$_2$], 1.87 [Quintuplet, 2H, CH$_2$], 3.47 [m, 6H, CH$_2$], 4.27 [t, 2H, CH$_2$—O], 6.48 [d, 1H, J=6.48 Hz, CH], 6.63 [dd, 1H, J$_p$=2.41 and J$_o$=8.95 Hz, CH], 7.33 [m, 2H, H$_{5,5''}$], 7.43 [d, 1H, J$_o$=8.95 Hz, CH], 7.84 [td, 2H, J=1.77 and J=7.71 Hz, H$_{4,4''}$], 7.97 [s, 2H, H$_{3',5'}$], 8.58 [dd, 2H, H$_{3,3''}$], 8.69 [dd, 2H, H$_{6,6''}$], 8.71 [s, 1H, CH], 8.86 [t, 1H, Amide].

6 TAMRA (6b):

δ 1.29 [s, 6H, CH$_3$], 1.32 [s, 6H, CH$_3$], 1.57 [Quintuplet, 2H, CH$_2$], 1.66 [Quintuplet, 2H, CH$_2$], 1.87 [Quintuplet, 2H, CH$_2$], 4.22 [t, 2H, CH$_2$—O], 3.42 [m, 2H, CH$_2$—NH], 6.38 [m, 1H, CH], 6.40 [m, 1H, CH], 6.47 [s, 1H, CH], 6.48 [s, 1H, CH], 6.58 [m, 1H, CH], 6.61 [m, 1H, CH], 7.31 [t, 2H, J=6.78 Hz, H$_{5,5''}$], 7.49 [s, 1H, CH], 7.85 [t, 2H, J=7.71 Hz, H$_{4,4''}$], 7.99 [s, 2H, H$_{3',5'}$], 8.04 [d, 1H, CH], 8.07 [d, 1H, CH], 8.61 [d, 2H, J=7.95 Hz, H$_{3,3''}$], 8.67 [d, 2H, J=4.50 Hz, H$_{6,6''}$].

LC Biotin (6c):

δ 1.54 [m, 4H, CH$_2$], 1.62 [m, 12H, CH$_2$], 1.92 [Quintuplet, 2H, CH$_2$], 2.20 [t, 4H, CH$_2$], 3.18 [t, 4H, CH$_2$—NH], 3.34 [m, 3H, CH—NH and CH$_2$—NH], 3.38 [m, 2H, CH$_2$—S], 4.32 [m, 4H, NH], 4.53 [m, 2H, CH—S], 7.55 [t, 2H, J=1.55 and 5.08, H$_{5,5''}$], 7.75 [s, 2H, H$_{3',5'}$], 8.05 [td, 2H, J=1.60 and 7.78 Hz, H$_{4,4''}$], 8.57 [d, 2H, J=7.96 Hz, H$_{3,3''}$], 8.69 [d, 2H, J=4.26 Hz, H$_{6,6''}$].

DNP (6d):

δ 1.20[m, 4H, CH$_2$], 1.50 [m, 2H, CH$_2$], 1.60 [m, 2H, CH$_2$], 1.76 [m, 2H, CH$_2$], 1.89 [m, 2H, CH$_2$], 2.22 [m, 4H, CH$_2$], 3.33 [m, 2H, CH$_2$—O], 3.37 [m, 2H, CH$_2$—NH], 4.27[broad peak, 1H, NH], 5.57 [m, 1H, NH], 7.37 [t, 2H, J=4.68 Hz, H$_{5,5''}$], 7.88 [t, 2H, J=7.02 Hz, H$_{4,4''}$], 7.98 [s, 2H, H$_{3',5'}$], 8.18 [dd, 1H, J$_m$=2.61 and J$_o$=9.48 Hz, CH], 8.47 [m, 1H, CH], 8.60 [d, 2H, J=7.83 Hz, H$_{3,3''}$], 8.67 [d, 2H, H$_{6,6''}$], 9.06 [d, 1H, J$_m$=2.64 Hz, CH].

$^{13}$C NMR (CDCl$_3$)

DEAC (6a):

δ 13.20 [CH$_3$, CH$_3$—CH$_2$], 24.29 [CH$_2$, CH$_2$—CH$_2$], 26.16 [CH$_2$, CH$_2$—CH$_2$—CH$_2$], 29.54 [CH$_2$, CH$_2$—CH$_2$—CH$_2$], 30.11 [CH$_2$, CH$_2$—NH], 40.33 [CH$_2$, CH$_2$—CH$_3$], 45.83 [CH$_2$, CH$_2$—CH$_3$], 68.84 [CH$_2$, O—CH$_2$], 108.33 [CH, C$_{3',5'}$], 110.68 [CH], 122.20 [CH, C$_{5,5''}$], 124.52 [CH, C$_{3,3''}$], 131.91 [CH], 137.50 [CH, C$_{4,4''}$], 148.88 [CH], 149.76 [CH, C$_{6,6''}$], 157.00 [C, C$_{2,2''}$], 157.76 [C, C$_{2',6'}$], 168.00 [C, C$_{4'}$], 173.00 [C, C=O amide].

| UV/Visible absorption (CHCl$_3$) | | |
|---|---|---|
| Compound | λ$_{max}$ (nm) | ε (M$^{-1}$·cm$^{-1}$) |
| 2  APET | 245 | 16500 |
|  | 279 | 16500 |
| 6a  DEAC APET | 250 | 1920 |
|  | 420 | 2480 |
| 6b  6 TAMRA APET | 255 | 45 700 |
|  | 276 | 37 800 |
|  | 545 | 660 |
| 6c  LC Biotin APET | 245 | 17 200 |
|  | 279 | 16 900 |
| 6d  DNP APET | 244 | 25 100 |
|  | 255 | 20 100 |
|  | 349 | 13 300 |

| Emission spectrum | | | |
|---|---|---|---|
| Compound | Concentration (mol/l) | Excitation | Emission maximum |
| 6a  DEAC APET | 3.6 · 10$^{-6}$ | 390 nm | 447.7 nm |
| 6b  6 TAMRA APET | 3.3 · 10$^{-6}$ | 510 nm | 556.7 nm |

Complexation of K$_2$PtCl$_4$ with 6c, LC Biotin, APET

K$_2$PtCl$_4$ (6.0 mg) was dissolved in N,N'-dimethylformamide (1 ml). The resulting solution was added slowly to a solution of DNP APET (8.3 mg) in N,N'-dimethylformamide (2 ml). The resulting solution was heated overnight at 40° C.

under protection from light. The mixture was then taken to dryness under reduced pressure.

$^{195}$Pt NMR (D$_2$O): $\delta_{Pt}$ −2701, and −2951 ppm.

Complexation of K$_2$PtCl$_4$ with 6d, DNP APET

K$_2$PtCl$_4$ (6.0 mg) was dissolved in N,N'-dimethylformamide (1 ml). The resulting solution was added slowly to a solution of DNP APET (9.3 mg) in propanol (1 ml) and N,N'-dimethylformamide (2 ml). The resulting solution was heated overnight at 40° C. under protection from light. The mixture was then taken to dryness under reduced pressure.

$^{195}$Pt NMR (D$_2$O): $\delta_{Pt}$ −2686, −2954 and −3442 ppm.

Additional Information on the Preparation of APET Complexes

4'-chloro 2,2':6',2" Terpyridine and 5-amino pentanol were purchased from Aldrich. K$_2$PtCl$_4$ was purchased from Sigma. The EZ Link NHS LC Biotin was purchased from Pierce. 6 TAMRA-SE, DNP-SE, DEAC were obtained from Molecular Probes. Column chromatography was carried out on silica gel 60 from Fluka for the ligand. The complexes were purified on Alumina N from ICN Biomedical GmbH. All the solvents were obtained from Merck and used without further purification. The water used was Milli Q water which is demineralized (R=18.2 MΩ/cm). The eluent used for all analytical runs by RP HPLC were:

A: 10% CH$_3$CN/90% TEAA 0.1M pH 5
B: 70% CH$_3$CN/30% TEAA 0.1M pH 5.

Buffer TEAA 1M pH 5.0: In a 500 ml graduate cylinder, 200 ml of Milli Q water, 30 ml of acetic acid and 70 ml of TEA were stirred. Then, Milli Q water was added up to 400 ml. The solution was cooled at room temperature and the pH was adjusted to 5 with acetic acid. The volume was adjusted with Milli Q to 500 ml. The solution was stored between 2 and 6° C.

Buffer Acetonitrile 10%/Triethylammonium acetate 0.1M pH 5.0 90%: In a 1000 ml graduate cylinder, 100 ml of acetonitrile, 90 ml of TEAA 1M pH 5.0 and 810 ml of Milli Q was stirred at room temperature. The solution was filtered on a membrane filter 1.0 μm. The solution was then degassed at a vacuum pump between 10 and 20 min. The buffer was stored between 2 and 6° C.

Buffer Acetonitrile 70%/Triethylammonium acetate 0.1M pH 5.0 30%:

In a 1000 ml graduate cylinder, 700 ml of acetonitrile, 30 ml of TEAA 1M pH 5.0 and 270 ml of Milli Q water was stirred at room temperature. The solution was filtered on a membrane filter 1.0 μm. The solution was then degassed at a vacuum pump between 10 and 20 min. The buffer was stored between 2 and 6° C.

Column: the RP HPLC analysis was carried out using Amersham Pharmacia Biotech Akta explorer equipped with a Phenomex Luna 5a C18(2) column. The characteristics of the column and of the analysis are following: Height 25 cm, Diameter 0.46 cm, Column volume 4.155 ml, Pressure 14 MPa, Flow rate 1 ml/min.

Wavelength: The analysis was generally performed with three wavelengths (254, 280 and 215 nm) but the wavelength were adapted for the fluorochrome in order to detect more easily the free fluorochrome (or hapten).

NMR: the compounds prepared were characterised by $^1$H NMR and $^{13}$C NMR spectroscopy. The $^1$H NMR was recorded at 300 MHz and $^{13}$C NMR at 75 MHz both on a Bruker DPX 300 spectrometer. $^1$H NMR spectrum were referenced to internal tetramethylsilane (TMS). $^{13}$C NMR spectrum were referenced on solvent resonance. All samples were measured at room temperature.

UV/Visible: UV spectra were recorded on Amersham Pharmacia Biotech Ultrospec 4000 spectrometer. The spectra were measured in a quartz cuvette between 200 and 700 nm for the ligand and the complex.

Emission spectrum: emission spectrum were recorded on a Perkin Elmer LS 45 Luminescence Spectrometer. The excitation wavelengths were selected with a monochromator. Each excitation wavelength have been chosen at the maximum absorption of the dye. The spectra have been recorded at room temperature.

IV. Use of APET-Pt/Pd/Ru/Co Reagents in Labelling of Nucleic Acids and Proteins

A variety of metals including platinum (Pt), palladium (Pd), ruthenium (Ru) and cobalt (Co) were introduced into the APET spacer. First, the fluorochrome or hapten was attached to APET and than a variety of metals was introduced in the labelled APET molecule. Chemical analysis was done by H-NMR. Purity of the RP-HPLC purified reagents varied from 80-99%.

Biotin-APET-Complexes:

Biotin-APET spacers were complexed with $Cd^{2+}$, $Co^{2+}$, $Cu^{2+}$, $Fe^{3+}$, $Mn^{2+}$, $Ni^{2+}$, $Pd^{2+}$, $Pt^{2+}$, $Ru^{2+}$ and $Zn^{2+}$. All complexes were soluble in water except Pt, Pd and Ru, these were soluble in DMF or DMSO. Purity of these reagents was 82-99% with >80% yield. The Bio-APET-Pd complex was less stable (possible explanation: formation of chains through the binding of Pd with thioether of biotin of another Bio-APET-Pd molecule, as could be seen in HPLC chromatograms). The labelling complexes were incubated with proteins and DNA at different ratios, temperatures, incubation time and pH. It was found that the Pt, Pd and Ru containing Bio-APET-complexes labelled both proteins and DNA, Bio-APET-Co labelled proteins (at pH≥8.0) but not DNA and the other metals were less reactive or did not form stable bonds.

FIG. 1 shows that Bio-APET-Ru is more reactive with DNA than the standard bidentate platinum labelling complex (Bio-BOC-Pt). DNA labelled faster and at significantly lower temperature. Also, when Bio-APET-Ru is mixed 1:1 with standard Flu-BOC-Pt, the majority of signal is found with biotin detection. If Flu-BOC-Pt was mixed with Bio-BOC-Pt the majority of signal is found with fluorescein detection. Bio-APET-Pt reacted similar to Bio-BOC-Pt (data not shown). Interestingly, methionine beads could be labelled with Pd and Pt containing APET complexes whereas the Bio-APET-Ru complex displayed much less, if any at all, reactivity towards methionine beads. Bio-APET-Ru was successfully used in a microarray experiment which included labelling of total RNA. In general, Bio-APET-Ru is more stable and outperforms the standard Biotin-BOC-Pt. Bio-APET-Ru is more reactive with both proteins and DNA (e.g. sufficient labelling at lower temperatures). Taking in consideration the fact that it is thought that Ru reacts only with nitrogen and not sulphur, Biotin-APET-Ru might be a more stable reagent than the standard Biotin-BOC-Pt complex (e.g. not sufficient labelling at lower temperatures).

Figure 2:
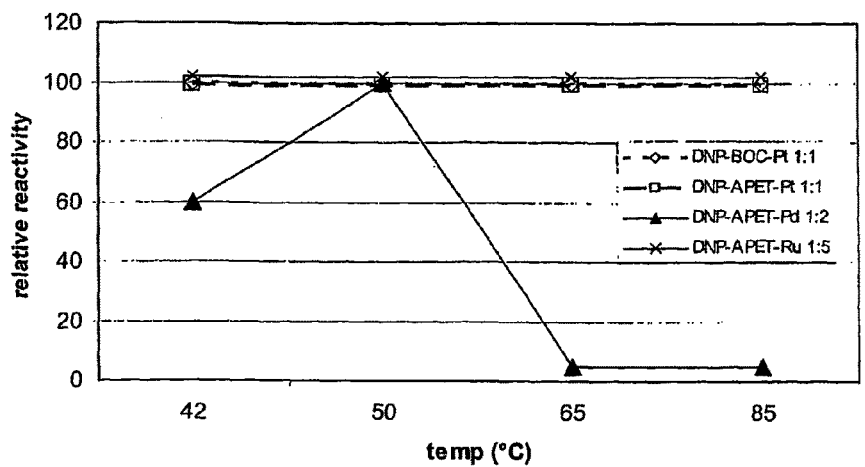
FIG. 2 depicts labelling of total human DNA (500-1500 bp) with DNP-BOC-Pt or DNP-APET-ULS. Temperatures as DNA labelling parameter. Direct spotting of labelled DNA and detection with anti-Biotin-AP (NBT/BCIP). Detection limit of standard DNP-ULS (3 pg) was set to 100% (relative reactivity).

DNP-APET-Complexes:

Pt, Pd and Ru containing DNP-APET complexes are reactive towards DNA and proteins (see table 1). As shown in FIG. 2 the reactivity for DNA at temp >40° C. is equal to the standard bidentate DNP-BOC-Pt. DNP-APET-Pd did not bind very stable to DNA as very few labelling is observed at temp >60° C.

Target labelling of whole human serum was performed using standard DNP-BOC-Pt and DNP-APET-Ru,Pt,Pd complexes. An IgA-, IgG- and IgM capture ELISA assay was developed. At the labelling ratios used with DNP-APET-Pt and -Pd most of the proteins quickly precipitated. The data shows that the Pt complex precipitated proteins faster, however labelled much worse than the Pd complex. No real positive results were found with DNP-APET-Pt. For IgG detection BOC-Pt=APET-Pd>APET-Ru and for IgA detection BOC-Pt=APET-Pd=APET-Ru. The DNP-APET-Pd can be optimized by lowering the ratio because at the lowest ratio used, only 20% IgG and 50% IgA were in solution (labelling 1 hr at 37° C.), whereas the best results obtained with control bidentate labelling complexes and DNP-APET-Ru were from fractions containing >85% IgG and >75% IgA (labelling 20 hrs at 37° C.).

Figure 3:
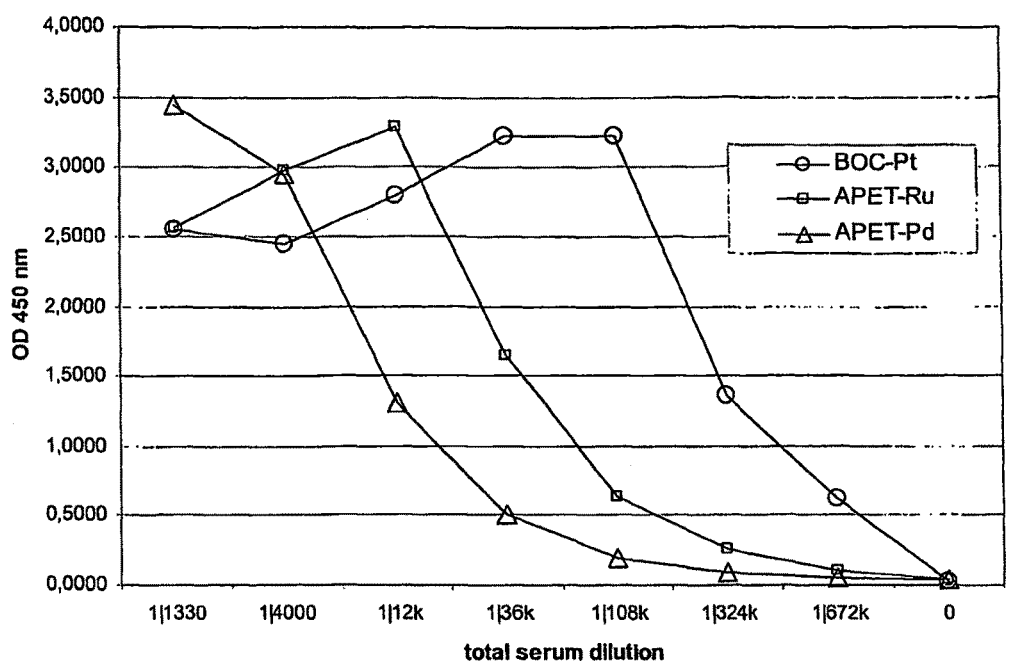
FIG. 3 depicts result of IgA capture ELISA of whole serum labelled with Cy5-labelling reagents.

Cy3/5-APET-Complexes:

Labelling of DNA was achieved with Cy3-APET-Pt, Cy5-APET-Pd and Cy5-APET-Ru. Target labelling of whole human serum was performed using standard Cy5-BOC-Pt, Cy5-APET-Ru and Cy5-APET-Pd. An IgA capture ELISA assay was developed. Cy5 served as a hapten (detected by HRP conjugated MoAb anti-Cy5). FIG. 3 shows that in all cases Cy5 labelled IgA is detected. Best results were obtained with the control Cy5-BOC-Pt complex.

V. Synthesis of a Peptide Marker-Tridentate-Pt Complex

The peptide was 16 amino acids long and serves as a shuttle molecule transporting a bio-molecule across the plasma membrane of a cell. The peptide has a terminal $NH_2$ group on one end and at the other end a solid support. Said amine was dissolved in a 50:50 mixture of MilliQ and ethanol to obtain a concentration of 0.02 mg of the amine per ml of solution. A 1000 fold molar equivalents of acrylonitrile was added to the solution. The solution was allowed to reflux (heat at 65° C.) overnight (reflux condenser fitted on top of the round bottom flask connected to a water cooling machine). The mixture was dried under rotary evaporation and the pellet was washed with dry ethanol (3-5 ml) and again evaporated to dryness. The nitrile compound was mixed with Nickel (II) chloride in a 1:1 molar ratio in dry ethanol (20 ml for 20 mmol of the nitrile). A freshly prepared solution of Sodium Borohydride (1 mmol per 1 mmol of nitrile) was added (2 mmol) very cautiously (in small portions) The solution was left stirring at room temperature for 2 hours. Next, the solution was filtered with MilliQ and the metallic Nickel was removed using a magnet. The filtrate was dissolved in 2 ml DMF. Five equivalents (100 μmol) of Potassium Tetrachloro Platinate (II) was added (powder) and the mixture was kept at 40° C. overnight. Next, the mixture filtered and washed with DMF (dimethyle formamide), MilliQ, and DCM (dichloro methane). The solution was taken to dryness under rotary evaporation. The solid support can be removed by standard chemistry depending on the type of chemistry used to couple the peptide to the solid support. In this particular case use was made of the TFA chemistry. Eventually, a mono-functional Pt complex was synthesized consisting of a transition metal-tridentate-(peptide) marker.

VI. Mass Tagging

Figure 4:
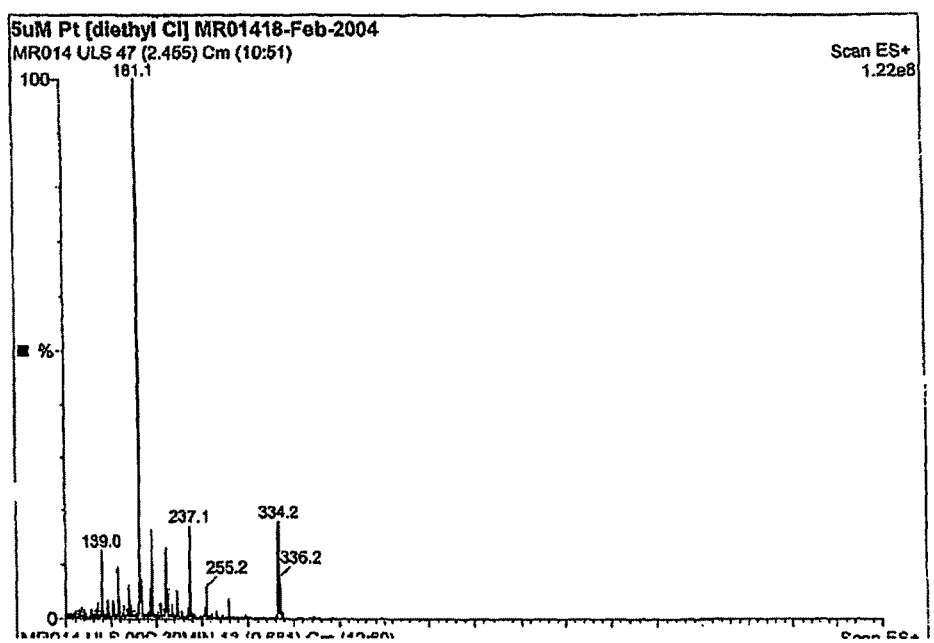
FIG. 4 depicts ESI-MS spectrum of Pt[dien Cl$^-$]Cl$^-$. The most abundant molecular ion obtained for the Pt[dien Cl$^-$]Cl$^-$ compound has a molecular ion [M1+] at m/z =334.

The diethylenetriamine Pt complex {Pt[dien Cl⁻] Cl⁻; 5 μM solution used} complex revealed that this compound was stable in MS and had an isotopic pattern characteristic of the simulated isotopic distributions of Pt and N. The most abundant molecular ion obtained for the light labelling compound (FIG. 4) has a molecular ion $[M^{1+}]$ at m/z=334. No contaminating peaks from the synthesis of this compound were observed. The only other peak visible was the loss of the Cl⁻ which was replaced with an OH⁻ group at m/z=315 observed during the labeling reaction.

Labeling of YGGFMK peptide with 3M excess of Pt[dienCl] Cl was performed at 45 and 85° C. After 1 hour incubation in 5 mM ammonium acetate pH 6-7, with 3M excess labeling compound: peptide, the methionine containing peptide was completely labeled at both temperatures. Labeling at 85° C. did not result in more side reaction products than labeling at 45° C. however the intensity of the side products was greater at 85 than at 45° C., but this can be attributed to the position of the nanospray capillary. This mono-functional tridentate labeling compound resulted in labeling of the peptide.

MS measurements were performed on a triple quadrupole instrument (Micromass, Manchester, U.K.) operating in positive ion mode, equipped with a Z-spray nanoelectrospray source. Nanoelectrospray needles were made from borosilicate glass capillaries (Kwik-Fil, World Precision Instruments, Sarasota, Fla.) on a P-97 puller (Sutter Instruments, Novato, Calif.). The needles were coated with a thin gold layer (approximately 500 Å) by using an Edwards Scancoat (Edwards Laboratories, Milpitas, Calif.) six Pirani 501 (at 40 mV, 1 kV, for 200 sec). The potential between the nanospray needle and the orifice of the mass spectrometer was typically set to 1,200 V; the cone voltage was 30 V. The nanospray needle was constantly kept at approximately 30° C. For MS/MS measurements, the collision energy was set to an appropriate voltage required to obtain sufficient sequence information (<20 V). Argon was used as collision gas. The quadrupole mass resolution parameters were set to a relatively large mass window to select the entire isotope envelope of the precursor ions.

VII. Synthesis of $N_3$ trans-C3 Tridentate (Scheme 5)

Preparation of 1-Michael Addition of Acrylonitrile:

N-Boc-hexane-1,6-diamine, (140.5 mg, 649.5 μmol) was dissolved in a mixture $H_2O$/EtOH 1/1 (20 ml). Acrylonitrile (425.5 μl, 6.495 mmol) was added to the resulting solution. The mixture was refluxed overnight at 60° C. and taken to dryness to afford pure an oily pale brown material. The residues were dissolved in $CH_2Cl_2$ and dried over $MgSO_4$. 1 was obtained following filtration and removal of the solvents under reduced pressure. (Yield: 166.8 mg, 95%).

$^1$H NMR ($CDCl_3$): δ 1.35 (4H, m, $NH(CH_2)_2(CH_2)_2$); 1.43 (13H, m, $NH(CH_2)(CH_2)CH_2)_2(CH_2)$+tBu); 2.60 (6H, m, $NH(CH_2)(CH_2)_3+(CH_2)(CH_2)CN$); 2.94 (4H, m, $CH_2CN$); 3.1 (2H, m, $(CH_2)NHBoc$); 4.55 (1H, broad peak, NHBoc).

Preparation of 2-Reduction with Lithium Aluminium Hydride:

1 (151.0 mg, 5.129*10⁻⁴ mol) was dissolved in dichloromethane (20 mL). The resulting solution was stirred in an ice bath (0° C.) for 20 minutes. Lithium aluminium hydride (5 mL of a 1 M solution in diethyl ether, 5 mmol) then was added. White solids were immediately observed to precipitate. The resulting mixture was stirred at 0° C. (ice bath) for 30 minutes during which the temperature was allowed to equilibrate with the ambient temperature. 7.5 mL of MilliQ then was cautiously added to neutralize the excess of lithium aluminium hydride. The addition of MilliQ caused the precipitation of a more important amount of white solids. The mixture then was filtered. The organic extracts were separated from the aqueous extracts and dried under reduced pressure yielding a colourless oil. (Yield: 23.5 mg, 15.1%).

$^1$H NMR of 1 ($CDCl_3$): $δ_H$ 1.22 (m, 4H, $CH_2$ from the hexanediamine spacer), 1.41 (m, 13H, $^t$Bu protons and remaining CH$_2$s from the hexanediamine spacer), 1.82 (broad singlet, 4H, NH$_2$), 2.29 (m, 8H, (CH$_2$)$_2$NH$_2$), 2.68 (m, 2H, NCH$_2$(CH$_2$)$_5$NHBoc), 3.06 (m, 2H, CH$_2$NHBoc), 4.61 (m, 2H, NHBoc) ppm. MS (ESP) m/z: 303 [M+H]$^+$.

Preparation of 3-Complexation with Potassium Tetrachloroplatinate:

2 (829.2 mg, 2.509 mmol) was dissolved in N,N'-dimethylformamide (535.4 mL). Potassium tetrachloroplatinate (1041.4 mg, 2.509 mmol) then was added in the solid state. The resulting mixture was heated at 40° C. overnight. The red platinum salts were observed to dissolve on heating. The mixture then was filtered to allow separation of the white potassium chloride solids. The filtrate was taken to dryness by heating under reduced pressure. MilliQ (about 30 mL) then was added to remove the remaining potassium chloride salts. The aqueous extracts were filtered. The brown solids were washed with diethyl ether (10 mL) and dried under reduced pressure. (Yield: 853.00 mg, 57.0%)

Preparation of 4a and In-Situ Preparation of 5-Removal of the Boc-Protecting Group and Reaction with the EZ-link-LC-Biotin Succinimidyl Ester:

3 (7.3 mg, 1.2*10$^{-5}$ mol) was mixed with 200 mM hydrochloric acid (4 mL). The resulting mixture was heated overnight at 50° C. The brown solids were observed to dissolve during the heating. The pH was adjusted to about 8.0 using solutions of sodium hydroxide (1 M) and hydrochloric acid (200 mM) in MilliQ.

Any insoluble brown material may be dissolved by the addition of the minimum amount of N,N'-dimethylformamide, via dropwise addition using a Pateur pipette. Alternatively, the addition of the succinimidyl ester in N,N'-dimethylformamide may enable solubilisation of the brown residues. MilliQ (476 µL), sodium hydroxide in MilliQ (1 M solution, 25 µL) then were added.

The EZ-link-LC-Biotin succinimidyl ester (4.76 mg, 1.0*10$^{-5}$ mol) in N,N'-dimethylformamide (95.2 µL) was added dropwise. MilliQ (381 µL), triethylamine (3 µL), MilliQ (162 µL), N,N'-dimethylformamide (4 drops via Pasteur Pipette addition), methanol (5 drops via Pasteur Pipette addition) and dichloromethane (4 drops) were added. The pH was verified to be around 8.0. Triethylamine may be added for this pH adjustment. The resulting mixture was stirred at ambient temperature wader protection from light for 5 minutes after which the pH was verified to be around 8.0.

Again, triethylamine may be employed for pH adjustment. The mixture was then stirred overnight at ambient temperature under protection from light. Insoluble materials then were filtered. The filtrate was taken to dryness.

Desalting can be achieved by removal of the solvents following the reaction with the succinimidyl ester. The residues are then dissolved in the minimum amount of MilliQ and the resulting solution is treated through a Sephadex G15 column.

$^{195}$Pt NMR (DMF-d$_7$): $\delta_{Pt}$ -3129 and -2519 ppm. MS (ESP) m/z: 800 [M]$^+$.

Use of N$_3$ Trans-Bio ULS (4a) in Protein Labeling

Figure 10:
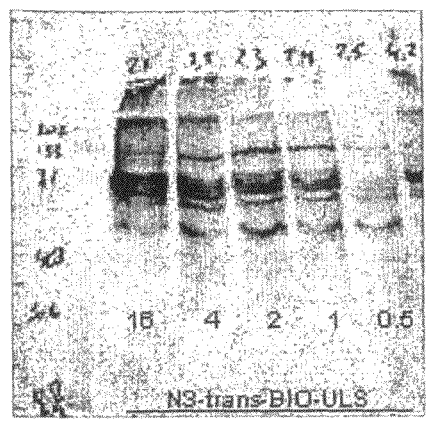
FIG. 10 depicts Western Blot of HELA lysate labeled with N3 trans-Bio ULS. From left to right, 0.5, 1, 2, 4, or 16 µg labeling compound per 50 µg protein, respectively.

A HELA cells lysate containing 50 µg proteins was labeled with compound 4a in 50 µl labeling buffer for 3 hours at 37° C. The amount of 4a was 0.5, 1, 2, 4 or 16 µg, respectively. The labeling reaction was stopped by addition of reducing sample buffer. BIO-AP was used as detection antibody (1:1000). The result of the Western blot is shown in FIG. 10.

Preparation of 4b and In-Situ Preparation of 5-Removal of the Boc-Protecting Group and Reaction with the 6-FAM Fluorescein Succinimidyl Ester:

3 (2.15 mg, 3.6*10$^{-5}$ mol) was mixed with 200 mM hydrochloric acid (366.46 µL). Methanol (3 drops via addition from a Pasteur Pipette) and N,N'-dimethylformamide then were added resulting in a total volume of about 1 mL.

The resulting mixture was heated overnight at 50° C. The brown solids were observed to dissolve during the heating. The pH of half of the solution then was adjusted to about 8.0 using solutions of sodium hydroxide (1 M) and hydrochloric acid (200 mM) in MilliQ. The succinimide coupling buffer (5*, 65.70 µL) then was added. Any insoluble brown material may be dissolved by the addition of the minimum amount of N,N'-dimethylformamide, via dropwise addition using a Pateur pipette. Alternatively, the addition of the succinimidyl ester in N,N'-dimethylformamide may enable solubilisation of the brown residues.

The fluorescein succinimidyl ester (0.82 mg, 2.1*10$^{-6}$ mol) in N,N'-dimethylformamide (164.235 µL) was added dropwise. The mixture was then stirred overnight at ambient temperature under protection from light. Desalting can be achieved by removal of the solvents following the reaction with the succinimidyl ester. The residues are then dissolved in the minimum amount of MilliQ and the resulting solution is treated through a Sephadex G15 column.

Figure 11:
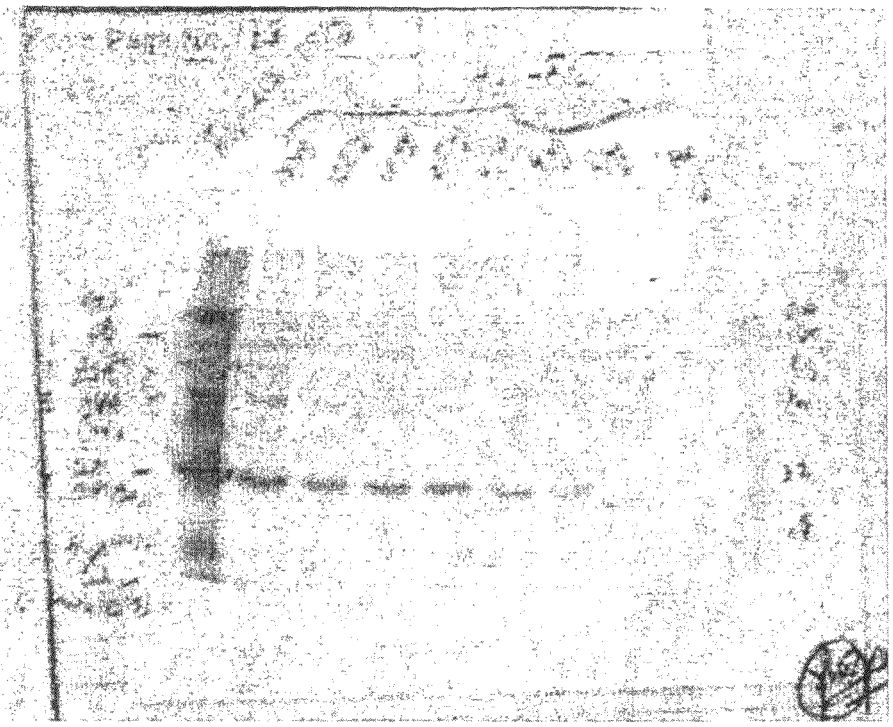
FIG. 11 depicts Western Blot of a mixture of six proteins labeled with N3 trans-Flu ULS (4b).
Figure 12:
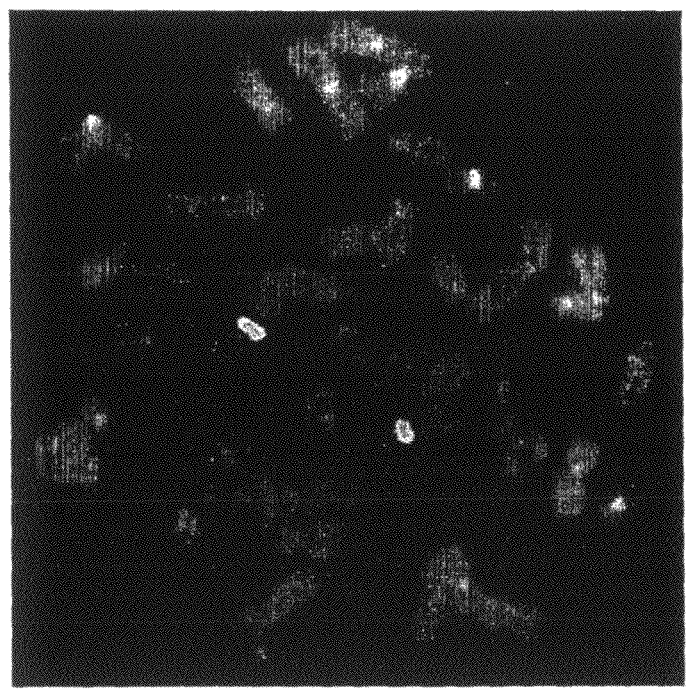
FIG. 12 depicts human metaphase hybridized with a 1.q12DNA probe labeled with $N_3$ trans-Flu ULS (4b); DNA is counterstained with DAPI.

Use of N$_3$ trans-Flu ULS (4b) in Protein Labeling 1, 2, 4, 6, 7.5, 10, 12.5, and 25 µg of 4b was used to label 50 µg of a six-protein mixture with different molecular weights (lactalbumin, trypsin inhibitor, carbonic anhydrase, ovalbumin, BSA, phosphorylase B). This labeling (one hour 50 C) was compared to standard labeling amounts of FLU-ULS at 12.5 µg on a blot detected with anti-FLU-AP (FIG. 11).

Labeling of Nucleic Acids with N$_3$ Trans-Flu ULS (4b)

DNA [a pUC19 plasmid with an 1.77 kb insert that carries the repetitive human satellite III DNA sequence located peri centromeric on chromosome 1 (1q12)] was labeled with 4b by adding 10 µg 4b to 3 µg of DNA in a volume of 100 µl. The mixture was incubated at 85° C. for 1 hour and unbound 4b was removed by standard ethanol precipitation. The DNA pellet showed green fluorescence when illuminated with UV light. Purified 4b labeled DNA was used as a probe in an in situ hybridization assay. The probe was dissolved in a hybridization buffer containing 60% formamide, 1×SSC and 10% dextran sulfate to a final concentration of 4 ng/µl. Ten µl were applied to a standard pretreated human metaphase preparation and incubated for 5 min. at 80° C. to allow both the target and the probe to denature. Next, slides were incubated overnight at 37° C. and unbound or poorly bound probe was removed by a wash in 1×SSC/0.1% SDS at 65° C. After re-hydration the preparation was embedded in an anti fading reagent containing DAPI. Fluorescence images were recorded using a Leica fluorescence microscope equipped with a digital camera.

FIG. 1 shows that the 4b labeled probe can be used to visualize the 1q12-region of human chromosome 12 by fluorescent in situ hybridization. The probe DNA labeling efficiency of 4b allows direct fluorescence visualization, even under stringent conditions.

Preparation of 4c and In-Situ Preparation of 5-Removal of the Boc-Protecting Group and Reaction with the DNP Succinimidyl Ester 3 (2.15 mg, 3.6*10$^{-5}$ mol) was mixed with 200 mM hydrochloric acid (163.62 µL). Methanol (3 drops via addition from a Pasteur Pipette) and N,N'-dimethylformamide then were added resulting in a total volume of about 1 mL.

The resulting mixture was heated overnight at 50° C. The brown solids were observed to dissolve during the heating. The pH of half of the solution then was adjusted to about 8.0 using solutions of sodium hydroxide (1 M) and hydrochloric acid (200 mM) in MilliQ. The succinimide coupling buffer (5*, 245.43 µL) then was added.

Any insoluble brown material may be dissolved by the addition of the minimum amount of N,N'-dimethylformamide, via dropwise addition using a Pateur pipette. Alternatively, the addition of the succinimidyl ester in N,N'-dimethylformamide may enable solubilisation of the brown residues. The DNP succinimidyl ester (1.6 mg, $3.34*10^{-6}$ mol) in N,N'-dimethylformamide (245.43 µL) was added dropwise. The mixture was then stirred overnight at ambient temperature under protection from light.

Desalting can be achieved by removal of the solvents following the reaction with the succinimidyl ester. The residues are then dissolved in the minimum amount of MilliQ and the resulting solution is treated through a Sephadex G15 column.

VIII. Synthesis of $N_3$ cis-C2 Tridentate (Scheme 6)

Preparation of 1-reaction with Chloroacetyl Chloride:

N-Boc-1,6-diaminohexane (175.6 mg, $8.12*10^{-4}$ mol) was dissolved in dichloromethane (15.4 mL). MilliQ (3883 µL) and a 1 M solution of sodium hydroxide (811.5 µL, $8.12*10^{-4}$ mol) in water. The resulting mixture was stirred 0° C. (ice bath) for 20 minutes.

Chloroacetyl chloride (64.5 µL, $8.10*10^{-4}$ mol) in dichloromethane (2940.40 µL) was added. The resulting mixture was stirred at 0° C. for 30 minutes.

The organic layer was then separated, dried over magnesium sulfate, filtered and dried under reduced pressure. White solids were obtained. (Yield: 161.4 mg, 67.9%).

$^1$H NMR of 1 (CDCl$_3$): $\delta_H$ 1.35 (m, 4H, CH$_2$ from the hexanediamine spacer), 1.44 (s, 9H, $^t$Bu protons), 1.53 (m, 4H, remaining CH$_2$s from the hexanediamine spacer), 3.10 (m, 2H, CH$_2$NHBoc), 3.26 (m, 2H, CH$_2$C(O)NHCH$_2$), 4.04 (s, 2H, CH$_2$C(O)), 4.52 (broad s, 1H, NHBoc), 6.61 (broad s, 2H, ClCH$_2$NHC(O)) ppm.

Preparation of 2-Reaction with Ethylenediamine:

Ethylenediamine (147.4 mg, 2.452 mmol) was taken-up in acetonitrile (25 mL). 1 (161.4 mg, $5.51*10^{-4}$ mol) was dissolved in acetonitrile (25 mL). The resulting solution was added at a rate of about 1 drop per 5 seconds to the ethylenediamine solution, at 75° C. After the addition was complete, the resulting mixture was heated at 75° C. overnight.

The solids then were filtered. The filtrate was taken to dryness. The insoluble materials were extracted in dichloromethane (3*3 mL). The organic extracts were separated from any aqueous residue and dried under reduced pressure, yielding a colourless oil. (Yield: 41.3 mg, 23.7%).

$^1$H NMR of 2 (CDCl$_3$): $\delta_H$ 1.09 (m, 4H, CH$_2$ from the hexanediamine spacer), 1.35 (s, 9H, $^t$Bu protons), 1.39 (m, 4H, remaining CH$_2$s from the hexanediamine spacer), 2.62 (t, 2H, J=7.14 Hz, NH$_2$CH$_2$), 2.91 (t, 2H, J=5.41 Hz, C(O)NHCH$_2$), 3.01 (m, 2H, CH$_2$NHBoc), 3.14 (broad s; 1H, NH, NHCH$_2$C(O)), 3.26 (t, J=5.36 Hz, 2H, NH$_2$CH$_2$CH$_2$), 3.40 (m, 2H, CH$_2$C(O)), 4.79 (broad s, 1H, NHBoc), 7.14 (broad s, 1H, CH$_2$C(O)NH) ppm.

Preparation of 3-Reduction with Lithium Aluminium Hydride:

2 (41.3 mg, $1.61*10^{-4}$ mol) was dissolved in dichloromethane (5 mL). The resulting solution was stirred in an ice bath (0° C.) for 20 minutes. Lithium aluminium hydride (1 mL of a 1 M solution in diethyl ether, 1 mmol) then was added. White solids were immediately observed to precipitate. The resulting mixture was stirred at 0° C. (ice bath) for 30 minutes during which the temperature was allowed to equilibrate with the ambient temperature. 1.5 mL of MilliQ then was cautiously added to neutralize the excess of lithium aluminium hydride. The addition of MilliQ caused the precipitation of a more important amount of white solids. The mixture then was filtered. The organic extracts were separated from the aqueous extracts and dried under reduced pressure yielding a colourless oil. (Yield: 33.8 mg, 69.4%).

$^1$H NMR of 3 (CDCl$_3$): $\delta_H$ 1.29 (m, 8H, CH$_2$ from the hexanediamine spacer), 1.41 (m, 9H, $^t$Bu protons), 1.80 (broad s, 4H, amine NH), 2.62 (m, 4H, NH$_2$CH$_2$ and NHCH$_2$ (CH$_2$)$_5$), 3.05 (m, 6H, NH$_2$CH$_2$CH$_2$NH(CH$_2$)$_2$NH), 3.21 (m, 2H, NHBoc) ppm.

Preparation of 4-Complexation with Potassium Tetrachloroplatinate:

3 (33.8 mg, $1.12*10^{-4}$ mol) was dissolved in N,N'-dimethylformamide (17.1 mL). Solid potassium tetrachloroplatinate (46.1 mg, $1.11*10^{-4}$ mol) was added. The resulting mixture was heated at 40° C. over the week-end. The red potassium tetrachloroplatinate solids were observed to dissolve during the heating and the N,N'-dimethylformamide solution was observed to turn pale brown. The solvents then were removed under pressure affording brown solids. The solids were washed with MilliQ (20 mL). The brown solids were dissolved again in N,N'-dimethylformamide (17.1 mL) and the resulting solution was heated at 40° C. overnight. The solvents then were removed under reduced pressure. Finally, the brown solids were dissolved in 47.2 mL of methanol and the resulting solution was heated at 60° C. over the week-end. (Yield: 34.3 mg, 59.8%).

$^{195}$Pt NMR (CD$_3$OD): $\delta_{Pt}$ −2523 ppm.

Preparation of 5 and In-Situ Preparation of 6-Removal of the Boc-Protecting Group and Reaction with the EZ-link-LC-Biotin Succinimidyl Ester:

4 (34.3 mg, $6.69*10^{-5}$ mol) was mixed with 200 mM hydrochloric acid (980.88 µL). The resulting mixture was heated overnight at 50° C. The brown solids were observed to dissolve during the heating. The pH was adjusted to about 8.0 using solutions of sodium hydroxide (1 M) and hydrochloric acid (200 mM) in MilliQ The resulting mixture was left to stand at ambient temperature for one hour. Any insoluble brown material may be dissolved by the addition of the minimum amount of N,N'-dimethylformamide, via dropwise addition using a Pateur pipette.

The EZ-link-LC-Biotin succinimidyl ester (21.1 mg, mol) in N,N-dimethylformamide (422 µL) was added dropwise. The pH was verified to be around 8.0. Triethylamine may be added for this pH adjustment. The resulting mixture was stirred at ambient temperature under protection from light for 5 minutes after which the pH was verified to be around 8.0. Again, triethylamine may be employed for pH adjustment. The mixture was then stirred overnight at ambient temperature under protection from light. (Yield: 15 mg, 27.8%)

Desalting can be achieved by removal of the solvents following the reaction with the succinimidyl ester. The residues are then dissolved in the minimum amount of MilliQ and the resulting solution is treated through a Sephadex G15 column.

$^{196}$Pt NMR (CD$_3$OD): $\delta_{Pt}$ −2630 ppm.

Use of $N_3$ cis-Bio ULS (5) as Labeling Compound

25 µg of a mixture of six proteins (see above) was labeled in 50 µl labeling buffer at 37° C. for 16 hours. The amount of 5 was 5, 10, 12.5, 15 or 20 µg, respectively. The labeling reaction was stopped by addition of a reducing sample buffer. Detection antibody: BIO-AP 1:1000.

Figure 14:
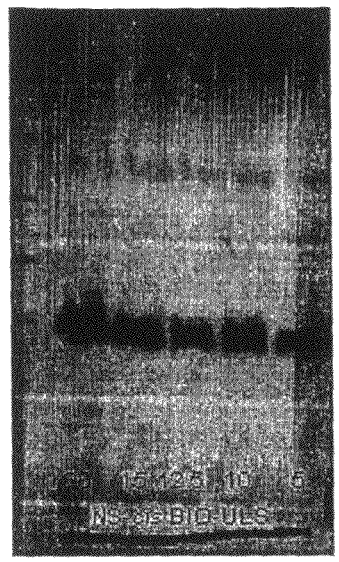
FIG. 14 depicts Western Blot of 6-protein mixture labeled with N3-cis Bio-ULS (5).

The results of the labeling are shown in FIG. 14.

Synthesis of 7-Complexation with Potassium Tetrachloroplatinate:

6c (5.8 mg, $8.6*10^{-6}$ mol) was dissolved in N,N'-dimethylformamide (11.2 mL). Solid potassium tetrachloroplatinate (3.6 mg, $8.8*10^{-6}$ mol) was added. The resulting mixture was heated at 40° C. overnight. The red potassium tetrachloroplatiziate solids were observed to dissolve during the heating and the N,N'-dimethylformamide solution was observed to turn orange. The solvents then were removed under pressure affording brown solids. (Yield: 12.4 mg, 37.4%).

$^1$H NMR of 1 (DMF-d$_7$): $\delta_H$ 1.27 (m, 4H, aliphatic CH$_2$s), 1.57 (m, 8H, aliphatic CH$_2$s), 1.88 (m, 4H, aliphatic CH$_2$s), 2.11 (m, 4H, C(O)CH$_2$), 3.11 (m, 4H, CH$_2$NHC(O)), 4.29 (m, 2H, CH$_2$NHC(O)NH), 4.61 (m, 2H, OCH$_2$), 7.50 (m, 2H, aromatic Hs), 7.80 (m, 2H, aromatic Hs), 8.69 (m, 4H, aromatic Hs) ppm. $^{195}$Pt NMR (DMF-d$_7$): $\delta_{Pt}$ −2707 ppm. MS (ESI$^+$) m/z: 867 [M]$^+$.

Figure 15:
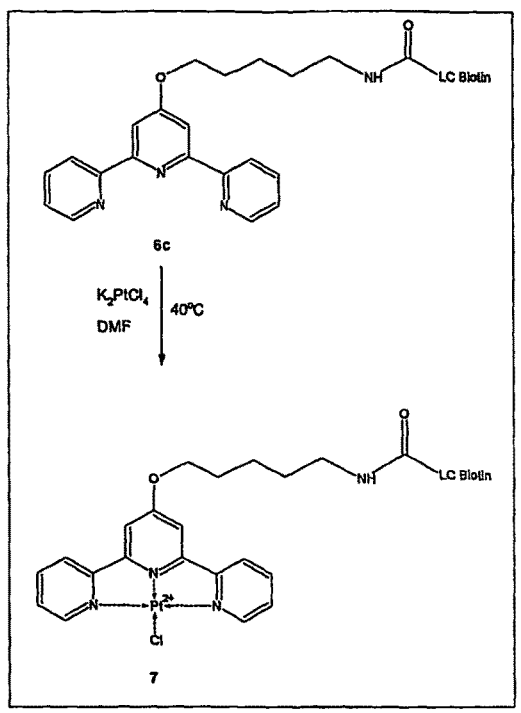
FIG. 15 depicts synthesis of 7-complexation with potassium tetrachloroplatinate.

FIG. 15 shows the synthesis scheme of 7—complexation with potassium tertachloroplatinate.

IX. Synthesis of N$_3$ trans-C2 Tridentate (Scheme 7)

Preparation of 1-Addition of Chloroacetonitrile:

N-Boc-1,6-diaminohexane (67.98 mg, 3.142*10$^{-4}$ mol) was taken-up in the minimum amount of dichloromethane (1 mL). Acetonitrile then was added (25 mL). Potassium carbonate (224.1 mg, 1.621 mmol) and potassium iodide (122.3 mg, 7.367*10$^{-4}$ mol) were also added, in the solid state. Chloroacetonitrile (1.0 mL, 16 mmol) then was added. The resulting mixture was heated at 75° C. overnight. The solution was observed to turn black during the heating. The solids then were filtered. The filtrate was taken to dryness. The insoluble materials were extracted in dichloromethane (3*3 mL). The organic extracts were combined, filtered and dried under reduced pressure. Orange solids were isolated.

$^1$H NMR of 1 (MeOD): $\delta_H$ 1.22 (m, 4l-1, CH$_2$ from the hexanediamine spacer), 1.36 (m, 13H, $^t$Bu protons and remaining CH$_2$s from the hexanediamine spacer), 2.63 (m, 2l-1, NCH$_2$(CH$_2$)$_5$NHBoc), 2.99 (m, 2H, CH$_2$NHBoc), 3.76 (m, 2H, CH$_2$CN), 6.49 (broad s, 1H, NHBoc) ppm.

Preparation of 2-Reduction with Lithium Aluminium Hydride:

1 (151.0 mg, 5.129*10$^{-4}$ mol) was dissolved in dichloromethane (20 mL). The resulting solution was stirred in an ice bath (0° C.) for 20 minutes. Lithium aluminium hydride (5 mL of a 1 M solution in diethyl ether, 6 mmol) then was added. White solids were immediately observed to precipitate. The resulting mixture was stirred at 0° C. (ice bath) for 30 minutes during which the temperature was allowed to equilibrate with the ambient temperature. 7.5 mL of MilliQ then was cautiously added to neutralize the excess of lithium aluminium hydride. The addition of MilliQ caused the precipitation of a more important amount of white solids. The mixture then was filtered. The organic extracts were separated from the aqueous extracts and dried under reduced pressure yielding a colourless oil. (Yield: 23.5 mg, 15.1%).

$^1$H NMR of 1 (CDCl$_3$): $\delta_H$ 1.22 (m, 4H, CH$_2$ from the hexanediamine spacer), 1.41 (m, 13H, $^t$Bu protons and remaining CH$_2$s from the hexanediamine spacer), 1.82 (broad singlet, 4H, NH$_2$), 2.29 (m, 8H, (CH$_2$)$_2$NH$_2$), 2.68 (m, 2H, NCH$_2$(CH$_2$)$_5$NHBoc), 3.06 (m, 2H, CH$_2$NHBoc), 4.61 (m, 2H, NHBoc) ppm. MS (ESI$^+$) m/z: 303 [M+H]$^+$.

Preparation of 3-Complexation with Potassium Tetrachloroplatinate:

2 (23.5 mg, 7.77*10$^{-5}$ mol) was dissolved in N,N'-dimethylformamide (12.5 mL). Solid potassium tetrachloroplatinate (32.4 mg, 7.80*10$^{-5}$ mol) was added. The resulting mixture was heated at 40° C. overnight. The red potassium tetrachloroplatinate solids were observed to dissolve during the heating and the N,N'-dimethylformamide solution was observed to turn pale brown. The solvents then were removed under pressure affording brown solids.

$^{195}$Pt NMR (DMF-d$_7$): $\delta_{Pt}$ −2586 ppm. (Yield: 27 mg, 61.1%)

Preparation of 4 and In-Situ Preparation of 5-Removal of the Boc-Protecting Group and Reaction with the EZ-link-LC-Biotin Succinimidyl Ester:

3 (13.5 mg, 4.13*10$^{-5}$ mol) was mixed with 200 mM hydrochloric acid (670.03 µL). The resulting mixture was heated overnight at 50° C. The brown solids were observed to dissolve during the heating. The pH was adjusted to about 8.0 using solutions of sodium hydroxide (1 M) and hydrochloric acid (200 mM) in MilliQ. Any insoluble brown material may be dissolved by the addition of the minimum amount of N,N'-dimethylformamide, via dropwise addition using a Pateur pipette. Alternatively, the addition of the succinimidyl ester in N,N'-dimethylformamide may enable solubilisation of the brown residues. The EZ-link-LC-Biotin succinimidyl ester (18.76 mg, 4.13*10$^{-5}$ mol) in N,N'-dimethylformamide (mL) was added dropwise. The pH was verified to be around 8.0. Triethylamine may be added for this pH adjustment. The resulting mixture was stirred at ambient temperature under protection from light for 5 minutes after which the pH was verified to be around 8.0. Again, triethylamine may be employed for pH adjustment. The mixture was then stirred overnight at ambient temperature under protection from light. Insoluble materials then were filtered.

Desalting can be achieved by removal of the solvents following the reaction with the succinimidyl ester. The residues are then dissolved in the minimum amount of MilliQ and the resulting solution is treated through a Sephadex G15 column.

$^{195}$Pt NMR (DMF-d$_7$): $\delta_{Pt}$ −2707 ppm. MS (ESP) m/z: 772 [M]$^+$.

X. Synthesis of NS$_2$ Trans-C2 Tridentate (Scheme 8)

Preparation of 1-Addition of 2-Chloroethylmethyl Ether:

N-Boc-1,6-diaminohexane (101.3 mg, 4.688*10$^{-4}$ mol) was taken-up in the minimum amount of dichloromethane (1 mL). Acetonitrile then was added (30 mL). Potassium carbonate (327.1 mg, 2.367 mmol) and potassium iodide (157.1 mg, 9.463*10$^{-4}$ mol) were also added, in the solid state. 2-chloroethylmethyl ether (93.3 µL, 9.35*10$^{-4}$ mol) then was added. The resulting mixture was heated at 75° C. overnight. The solids then were filtered. The filtrate was taken to dryness. The residues were extracted with dichloromethane (3*3 mL). The organic extracts were combined, filtered and dried under reduced pressure, yielding white solids. (Yield: 19.2 mg, 11.2%).

$^1$H NMR of 1 (CDCl$_3$): $\delta_H$ 1.27 (m, 4H, CH$_2$ from the hexanediamine spacer), 1.40 (m, 9H, $^t$Bu protons), 1.44 (m, 4H, remaining CH$_2$s from the hexanediamine spacer), 2.10 (s, 6H, CH$_3$), 2.54 (m, 6H, NCH$_2$(CH$_2$)$_3$NHBoc and NCH$_2$CH$_2$S), 2.76 (m, 2H, CH$_2$NHBoc), 3.21 (m, 2H, NHBoc), 4.54 (broad s, 1H, NHBoc) ppm. MS (ESP) ink: 365 [M+H]$^+$.

Preparation of 2-Complexation with Potassium Tetrachloroplatinate:

1 (19.2 mg, 5.26*10$^{-5}$ mol) was dissolved in N,N'-dimethylformamide (11.2 mL). Solid potassium tetrachloroplatinate (21.7 mg, 5.23*10$^{-5}$ mol) was added. The resulting mixture was heated at 40° C. overnight. The red potassium tetrachloroplatinate solids were observed to dissolve during the heating and the N,N'-dimethylformamide solution was observed to turn orange. The solvents then were removed under pressure affording brown solids. (Yield: 12.4 mg, 37.4%).

$^{195}$Pt NMR (DMF-d$_7$): $\delta_{Pt}$ −3543 ppm.

Preparation of 3 and In-Situ Preparation of 4-Removal of the Boc-Protecting Group and Reaction with the EZ-link-LC-Biotin Succinimidyl Ester:

2 (12.4 mg, 1.97*10$^{-5}$ mol) was mixed with 200 mM hydrochloric acid (1336.39 µL). The resulting mixture was heated overnight at 50° C. The brown solids were observed to dissolve during the heating. The pH was adjusted to about 8.0 using solutions of sodium hydroxide (1 M; 240 μL) and hydrochloric acid (200 mM; 10 μL) in MilliQ. Any insoluble brown material may be dissolved by the addition of the minimum amount of N,N'-dimethylformamide, via dropwise addition using a Pateur pipette. Alternatively, the addition of the succinimidyl ester in N,N'-dimethylformamide may enable solubilisation of the brown residues.

The EZ-link-LC-Biotin succinimidyl ester (7.993 mg, $1.76*10^{-5}$ mol) in N,N'-dimethylformamide (159.86 μL) was added dropwise. The pH was verified to be around 8.0. Triethylamine may be added for this pH adjustment. The resulting mixture was stirred at ambient temperature under protection from light for 5 minutes after which the pH was verified to be around 8.0. Again, triethylamine may be employed for pH adjustment. The mixture was then stirred overnight at ambient temperature under protection from light. Insoluble materials then were filtered. Purification was performed using HPLC. The target species was found to elute in Fraction 10 (57.94 to 62.94 mL).

Desalting can be achieved by removal of the solvents following the reaction with the succinimidyl ester. The residues are then dissolved in the minimum amount of MilliQ and the resulting solution is treated through a Sephadex G15 column.

$^1$H NMR of 1 (D$_2$O): $\delta_H$ 1.62 (m, 12H, from the LC-Biotin spacer), 1.77 (m, 8H, CH$_2$s from the hexanediamine spacer), 2.94 (m, 4H, C(O)CH$_2$), 3.05 (s, 6H, CH$_3$), 3.30 (m, 6H, NCH$_2$(CH$_2$)$_5$NH and NCH$_2$CH$_2$s), 3.54 (m, 4H, NCH$_2$CH$_2$s), 3.86 (m, 2H, CH$_2$C(O)NH), 4.0 (m, 2H, CH$_2$NHC(O)NH) ppm.

MS (ESI$^+$) m/z: 782 [M$^+$−Cl$^-$+OH$^-$]$^+$.

Details on Preparative HPLC Analysis Method:

Analytical HPLC analysis was performed on a reversed phase Luna3 C18 column of a volume of 88.247 mL (250*21.2 uL), with NaCl (100 mM; 90% in buffer A and 70% in buffer B)/2-propanol (10% in buffer A and 90% in buffer B) buffers. 803.0 mL (approximately) in total were eluted through the column at a rate of 5.0 mL/minute. The method incorporated a linear gradient between 94.25 and 182.49 mL (1.0 column volume) to reach a concentration of 30.0% B, between 182.49 and 403.21 mL (2.5 column volumes) to attain a concentration of 80% B, between 403.21 and 447.33 mL (0.5 column volume) to attain a concentration of 100% B and between 579.91 mL and 624.03 mL (0.5 column volume) to elute pure A again. Between 447.33 and 579.81, pure B was eluted.

What is claimed is:

1. A labeled transition metal complex comprising a transition metal atom, a reactive moiety for allowing a chemical or biological entity to become attached to the transition metal atom, an inert tridentate moiety as a stabilizing bridge, and a marker, wherein the transition metal is chosen from the group consisting of vanadium, chromium, iron, ruthenium, palladium, platinum, molybdenum, tungsten, cobalt, manganese, osmium, rhodium, iridium, zinc, and cadmium; wherein the marker is separated from the tridentate moiety by means of a spacer, wherein the spacer comprises a chain having between 4 and 20 atoms selected from carbon, nitrogen, and oxygen.

2. A complex according to claim 1, wherein the transition metal is chosen from the group consisting of iron, nickel, ruthenium, palladium, platinum, molybdenum, tungsten, and cobalt.

3. A complex according to claim 2, wherein the transition metal is platinum, cobalt, or ruthenium.

4. A complex according to of claim 1, wherein the transition metal atom is attached to the tridentate moiety by means of three donor atoms, each being independently selected from the group of nitrogen, oxygen, sulphur, and phosphorus atoms, which donor atoms are present in the tridentate moiety.

5. A complex according to claim 4, wherein the transition metal atom is attached to the tridentate moiety by means of three nitrogen atoms.

6. A complex according to claim 4, wherein the donor atoms in the tridentate moiety are separated from each other by 1 to 5, preferably 1 to 3 atoms.

7. A complex according to claim 1, wherein the marker is a fluorescent label.

8. A complex according to claim 1, wherein the reactive moiety is chosen from the group consisting of Cl$^-$, NO$_3^-$, HCO$_3^-$, CO$_3^{2-}$, SO$_3^{2-}$, ZSO$^{3-}$, I$^-$, Br$^-$, F$^-$, acetate, carboxylate, phosphate, ethylnitrate, oxalate, citrate, a phosphonate, ZO$^-$, and water wherein Z represents a hydrogen moiety or an alkyl or aryl group having from 1 to 10 carbon atoms.

9. A labeled chemical or biological entity comprising a chemical or biological entity which is attached to a transition metal complex as defined in claim 1, wherein the chemical or biological entity has replaced the reactive moiety.

10. A labeled chemical or biological entity according to claim 9, wherein the entity is selected from the group consisting of amino acids, peptides, oligopeptide, polypeptides, proteins, immunoglobulins, enzymes, synzymes, phospholipides, glycoproteins, nucleic acids, nucleosides, nucleotides, oligonucleotides, polynucleotides, peptide nucleic acids, peptide nucleic acid oligomers, peptide nucleic acid polymers, amines and aminoglycosides.

11. A set of at least two transition metal complexes of different molecular weight, wherein each of said transition metal complexes is as defined in claim 1.

* * * * *